United States Patent
Imamura et al.

(10) Patent No.: US 8,210,035 B2
(45) Date of Patent: Jul. 3, 2012

(54) COLLECTION MEDIUM AND COLLECTION AMOUNT MEASURING APPARATUS, AND MEASURING METHOD, PROGRAM, AND RECORDING MEDIUM OF THE SAME

(75) Inventors: Motoki Imamura, Miyagi (JP); Shigeki Nishina, Miyagi (JP)

(73) Assignee: Advantest Corporation, Tokyo (JP)

( * ) Notice: Subject to any disclaimer, the term of this patent is extended or adjusted under 35 U.S.C. 154(b) by 255 days.

(21) Appl. No.: 12/608,282

(22) Filed: Oct. 29, 2009

(65) Prior Publication Data

US 2011/0094300 A1   Apr. 28, 2011

(30) Foreign Application Priority Data

Oct. 28, 2009   (JP) .................................. 2009-247782

(51) Int. Cl.
*G01M 15/00* (2006.01)

(52) U.S. Cl. .................. 73/114.75; 73/32 R; 73/863.23; 73/863.71; 55/502; 55/503

(58) Field of Classification Search .................... 73/149, 73/32 A, 31.07, 28.01, 28.04; 55/423, 502, 55/523

See application file for complete search history.

(56) References Cited

U.S. PATENT DOCUMENTS

| | | | | |
|---|---|---|---|---|
| 4,420,316 A | * | 12/1983 | Frost et al. | 55/523 |
| 4,509,966 A | * | 4/1985 | Dimick et al. | 55/502 |
| 2005/0102987 A1 | * | 5/2005 | Kudo | 55/523 |

FOREIGN PATENT DOCUMENTS

| | | |
|---|---|---|
| JP | 6-288220 | 10/1994 |
| JP | 2009-2276 | 1/2009 |
| JP | 2009-57948 | 3/2009 |
| WO | 2009/031600 | 3/2009 |

OTHER PUBLICATIONS

English language Abstract of JP 6-288220, Oct. 11, 1994.
English language Abstract of JP 2009-2276, Jan. 8, 2009.
English language Abstract of JP 2009-57948, Mar. 19, 2009.

* cited by examiner

*Primary Examiner* — Lisa Caputo
*Assistant Examiner* — Roger Hernandez-Prewitt
(74) *Attorney, Agent, or Firm* — Greenblum & Bernstein, P.L.C.

(57) ABSTRACT

The present invention precisely measures characteristic values (such as the absorption coefficient) of an electromagnetic wave when a density of a PM in a DPF which collects the PM in an exhaust gas. The DPF receives the exhaust gas, and collects the PM in the exhaust gas. The DPF includes first hole portions which are open at a first end on a side for receiving the exhaust gas, and are closed at a second end on a side opposite to the first end, second hole portions which are closed at the first end and are open at the second end, and third hole portions which are closed at the first end. The first hole portion and the second hole portion are adjacent to each other. The third hole portions are adjacent to each other. The PM in the exhaust gas passing through partition walls which partition the first hole portion and the second hole portion adjacent to each other is collected by the partition walls.

24 Claims, 16 Drawing Sheets

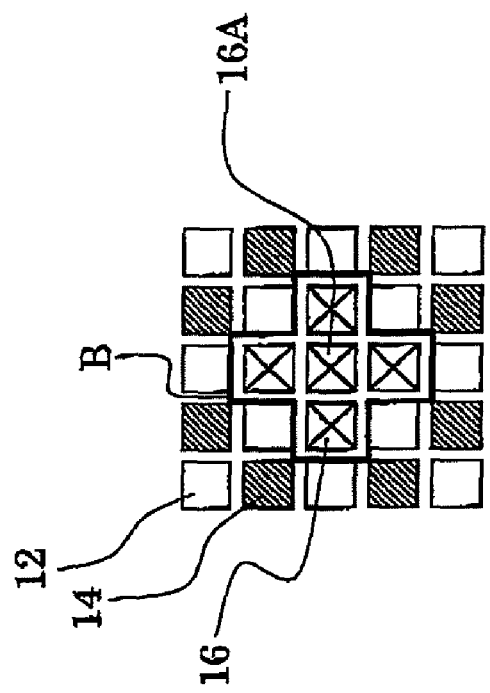
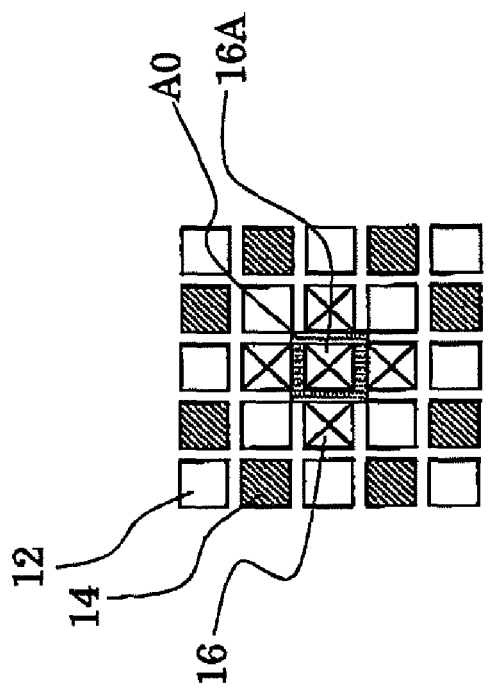
Fig. 4

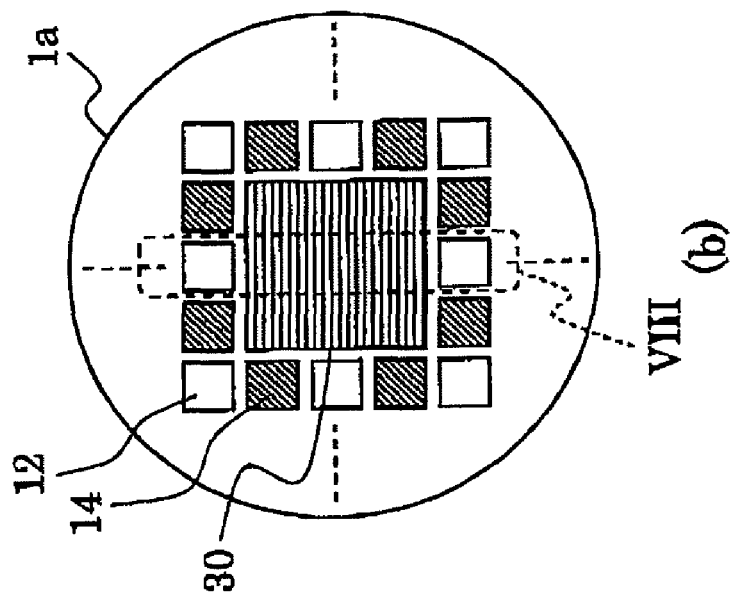
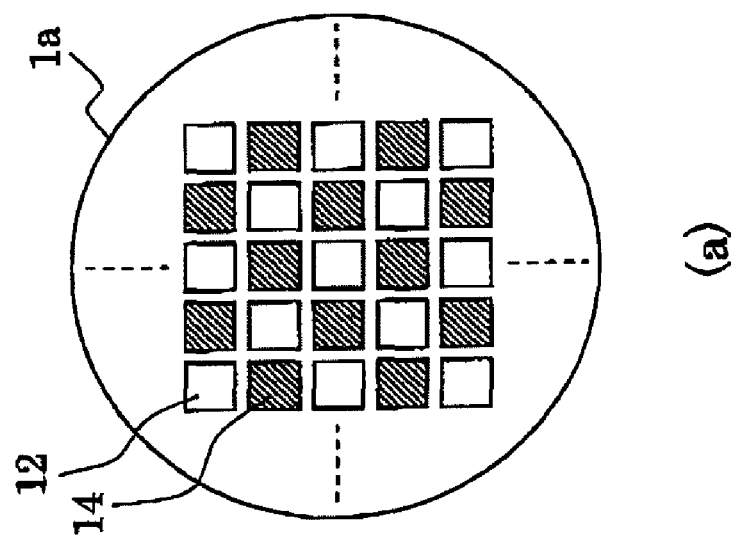
Fig. 7

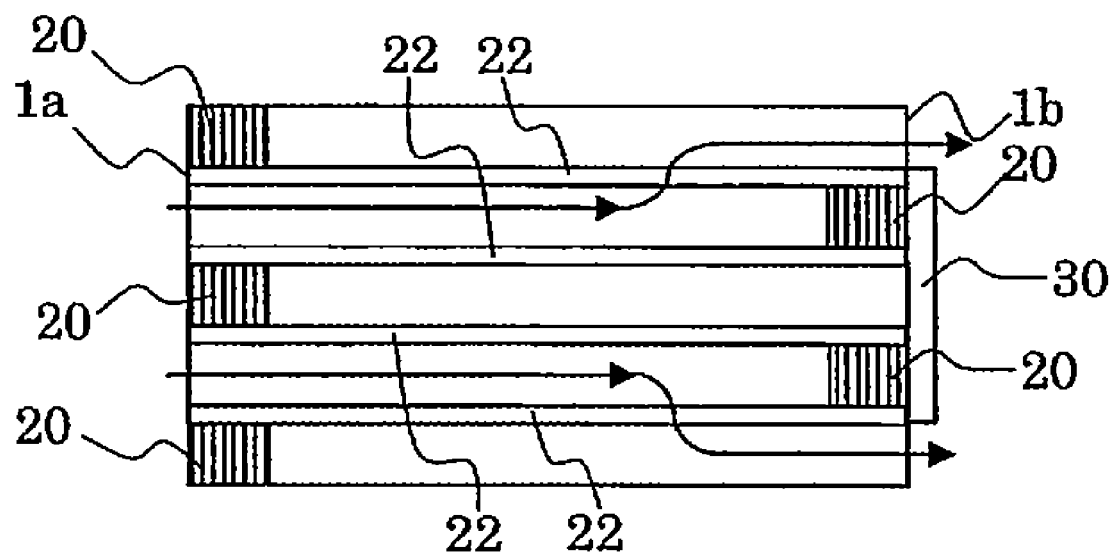
Fig. 12

COLLECTION MEDIUM AND COLLECTION AMOUNT MEASURING APPARATUS, AND MEASURING METHOD, PROGRAM, AND RECORDING MEDIUM OF THE SAME

BACKGROUND ART

1. Field of the Invention

The present invention relates to measurement of a density of a particulate matter (such as soot made of carbon particles, high molecular hydrocarbon particles, and sulfur particles such as sulfate) in a collector of the particulate matter using an electromagnetic wave (frequency thereof is equal to or more than 0.01 [THz], and equal to or less than 100 [THz]) (such as a terahertz wave (frequency thereof is equal to or more than 0.03 [THz], and equal to or less than 10 [THz]), for example).

2. Description of the Prior Art

It has conventionally been known to measure the quantity or density of a particulate matter in a particulate collection filter referred to as a diesel particulate filter (DPF) for a diesel engine (or for particulate collection and combustion catalyst for a diesel engine) using an electromagnetic wave including a terahertz wave or micro wave (refer to Patent Documents 1, 2 and 3).

According to the above-mentioned conventional technologies, the intensity of the electromagnetic wave which has transmitted through the DPF (or combustion catalyst) is measured, the absorption coefficient $\alpha'$ of the electromagnetic wave is derived, and the density (or quantity) of the particulate matter is measured. Moreover, the absorption coefficient $\alpha 0'$ of the electromagnetic wave when the density of the particulate matter is zero, and an increase rate $\beta'$ of the absorption coefficient of the electromagnetic wave with respect to the density of the particulate matter are measured in advance. The density of the particulate matter is represented by $(\alpha'-\alpha 0')/\beta'$, and the density of the particulate matter can thus be obtained.

The DPF itself absorbs the electromagnetic wave, and $\alpha 0'>0$ thus holds. Therefore, it is conceived that the absorption coefficient of the electromagnetic wave of the DPF when it is new (without adhered particulate matter, of course) is measured, and the measurement value is set to $\alpha 0'$.

(Patent Document 1) Japanese Laid-Open Patent Publication (Kokai) No. H6-288220
(Patent Document 2) Japanese Laid-Open Patent Publication (Kokai) No. 2009-2276
(Patent Document 3) Japanese Laid-Open Patent Publication (Kokai) No. 2009-57948

SUMMARY OF THE INVENTION

However, there are possibly individual differences in $\alpha 0$ among DPFs. In other words, $\alpha 0'$ of the individual DPFs are not the same. Moreover, $\alpha 0'$ possibly changes due to a passage of time. Consequently, the absorption coefficient of the electromagnetic wave of a new DPF may be different from $\alpha 0'$ of a DPF on which the density of the particulate matter is to be measured.

It is therefore an object of the present invention to precisely measure characteristic values (such as the absorption coefficient) of the electromagnetic wave when the density of a material in a collector for collecting the material in a gas takes a predetermined value such as zero.

According to the present invention, a first collector which receives a gas, and collects a material in the gas includes: a first hole portion that is open at a first end on a side for receiving the gas, and is closed at a second end on a side opposite to the first end; a second hole portion that is closed at the first end, and is open at the second end; and a third hole portion that is closed at the first end, wherein: the first hole portion and the second hole portion are adjacent to each other; the third hole portions are adjacent to each other; and the material in the gas passing through the a partition wall partitioning the first hole portion and the second hole portion adjacent to each other is collected by the partition wall.

According to the thus constructed first collector which receives a gas, and collects a material in the gas, a first hole portion is open at a first end on a side for receiving the gas, and is closed at a second end on a side opposite to the first end. A second hole portion is closed at the first end, and is open at the second end. A third hole portion is closed at the first end. The first hole portion and the second hole portion are adjacent to each other. The third hole portions are adjacent to each other. The material in the gas passing through the a partition wall partitioning the first hole portion and the second hole portion adjacent to each other is collected by the partition wall.

According to the present invention, a second collector which receives a gas, and collects a material in the gas includes: a first hole portion that is open at a first end on a side for receiving the gas, and is closed at a second end on a side opposite to the first end; a second hole portion that is closed at the first end, and is open at the second end; and a third hole portion that is closed at the second end, wherein: the first hole portion and the second hole portion are adjacent to each other; the third hole portions are adjacent to each other; and the material in the gas passing through the a partition wall partitioning the first hole portion and the second hole portion adjacent to each other is collected by the partition wall.

According to the thus constructed second collector which receives a gas, and collects a material in the gas, a first hole portion is open at a first end on a side for receiving the gas, and is closed at a second end on a side opposite to the first end. A second hole portion is closed at the first end, and is open at the second end. A third hole portion is closed at the second end. The first hole portion and the second hole portion are adjacent to each other. The third hole portions are adjacent to each other. The material in the gas passing through the a partition wall partitioning the first hole portion and the second hole portion adjacent to each other is collected by the partition wall.

According to the present invention, a third collector which receives a gas, and collects a material in the gas includes: a first hole portion that is open at a first end on a side for receiving the gas, and is closed at a second end on a side opposite to the first end; a second hole portion that is closed at the first end, and is open at the second end; and a third hole portion that is closed between the first end and the second end, wherein: the first hole portion and the second hole portion are adjacent to each other; the third hole portions are adjacent to each other; and the material in the gas passing through the a partition wall partitioning the first hole portion and the second hole portion adjacent to each other is collected by the partition wall.

According to the thus constructed third collector which receives a gas, and collects a material in the gas, a first hole portion is open at a first end on a side for receiving the gas, and is closed at a second end on a side opposite to the first end. A second hole portion is closed at the first end, and is open at the second end. A third hole portion is closed between the first end and the second end. The first hole portion and the second hole portion are adjacent to each other. The third hole portions are adjacent to each other. The material in the gas passing through the a partition wall partitioning the first hole portion and the second hole portion adjacent to each other is collected by the partition wall.

According to the first, second or third collector of the present invention, the third hole portion may be closed by a plug provided inside the third hole portion.

According to the first or second collector of the present invention, the third hole portion may be closed by a closing member in contact with an end surface of the first end or an end surface of the second end.

According to the present invention, a fourth collector which receives a gas, and collects a material in the gas includes: a first hole portion that is open at a first end on a side for receiving the gas, and is closed at a second end on a side opposite to the first end; and a second hole portion that is closed at the first end, and is open at the second end, wherein: the first hole portion and the second hole portion are adjacent to each other; a partition wall which partitions between the first hole portion and the second hole portion adjacent to each other is an partition wall easy to pass which is easy for the gas to pass through or a partition wall hard to pass which is hard for the gas to pass through; and the material in the gas passing through the partition wall is collected by the partition wall.

According to the thus constructed fourth collector which receives a gas, and collects a material in the gas, a first hole portion is open at a first end on a side for receiving the gas, and is closed at a second end on a side opposite to the first end. A second hole portion is closed at the first end, and is open at the second end. The first hole portion and the second hole portion are adjacent to each other. A partition wall which partitions between the first hole portion and the second hole portion adjacent to each other is an partition wall easy to pass which is easy for the gas to pass through or a partition wall hard to pass which is hard for the gas to pass through. The material in the gas passing through the partition wall is collected by the partition wall.

According to the fourth collector of the present invention, the partition wall easy to pass may be higher in porosity than the partition wall hard to pass.

According to the fourth collector of the present invention, the partition wall hard to pass may not pass the gas.

According to the first, second or third collector of the present invention, a line segment which is an intersection portion of a line perpendicular to an extension direction of the first, second, and third hole portions and the collector may be on a side of the third hole portion with respect to a border between the third hole portion and the first or second hole portion.

According to the fourth collector of the present invention, a line segment which is an intersection portion of a line perpendicular to an extension direction of the first and second hole portions and the collector passes through the first hole portion adjacent to the second hole portion via only the partition wall hard to pass and the second hole portion adjacent to the first hole portion via only the partition wall hard to pass, and does not pass through the first hole portion adjacent to the second hole portion via the partition wall easy to pass and the second hole portion adjacent to the first hole portion via the partition wall easy to pass.

According to the first, second, third or fourth collector of the present invention, the collector may be cylindrical; and the line may intersect with an axis of the center of rotation of the collector.

According to the present invention, a first collection quantity measurement device includes: an electromagnetic wave output device that outputs an electromagnetic wave to be measured at a frequency equal to or higher than 0.01 [THz] and equal to or lower than 100 [THz] toward the first, second or third collector of the present invention; an electromagnetic wave detector that detects the electromagnetic wave to be measured which has transmitted through the collector; a reference value deriving unit that derives, based on a result detected by the electromagnetic wave detector, any one of an absorption rate, a group delay, and a dispersion of the electromagnetic wave to be measured in a reference area; and a collection quantity deriving unit that derives, based on the result detected by the electromagnetic wave detector and the result derived by the reference value deriving unit, a weight or a density of the material present in an collection area, wherein: the reference area includes the third hole portion adjacent only to the third hole portion, and is on a side of the third hole portion with respect to a border between the third hole portion and the first or second hole portion; and the collection area is an area of the collector except for the reference area.

According to the thus constructed first collection quantity measurement device, an electromagnetic wave output device outputs an electromagnetic wave to be measured at a frequency equal to or higher than 0.01 [THz] and equal to or lower than 100 [THz] toward the first, second or third collector of the present invention. An electromagnetic wave detector detects the electromagnetic wave to be measured which has transmitted through the collector. A reference value deriving unit derives, based on a result detected by the electromagnetic wave detector, any one of an absorption rate, a group delay, and a dispersion of the electromagnetic wave to be measured in a reference area. A collection quantity deriving unit derives, based on the result detected by the electromagnetic wave detector and the result derived by the reference value deriving unit, a weight or a density of the material present in an collection area. The reference area includes the third hole portion adjacent only to the third hole portion, and is on a side of the third hole portion with respect to a border between the third hole portion and the first or second hole portion; and the collection area is an area of the collector except for the reference area.

According to the present invention, a second collection quantity measurement device includes: an electromagnetic wave output device that outputs an electromagnetic wave to be measured at a frequency equal to or higher than 0.01 [THz] and equal to or lower than 100 [THz] toward the fourth collector of the present invention; an electromagnetic wave detector that detects the electromagnetic wave to be measured which has transmitted through the collector; a reference value deriving unit that derives, based on a result detected by the electromagnetic wave detector, any one of an absorption rate, a group delay, and a dispersion of the electromagnetic wave to be measured in a reference area; and a collection quantity deriving unit that derives, based on the result detected by the electromagnetic wave detector and the result derived by the reference value deriving unit, a weight or a density of the material present in an collection area, wherein: the reference area includes the first hole portion or the second hole portion enclosed by the partition wall hard to pass; and the collection area is an area of the collector except for the reference area.

According to the thus constructed second collection quantity measurement device, an electromagnetic wave output device outputs an electromagnetic wave to be measured at a frequency equal to or higher than 0.01 [THz] and equal to or lower than 100 [THz] toward the fourth collector of the present invention. An electromagnetic wave detector detects the electromagnetic wave to be measured which has transmitted through the collector. A reference value deriving unit derives, based on a result detected by the electromagnetic wave detector, any one of an absorption rate, a group delay, and a dispersion of the electromagnetic wave to be measured in a reference area. A collection quantity deriving unit derives, based on the result detected by the electromagnetic wave detector and the result derived by the reference value deriving unit, a weight or a density of the material present in an collection area. The reference area includes the first hole portion or the second hole portion enclosed by the partition wall hard to pass. The collection area is an area of the collector except for the reference area.

According to the present invention, the first or second collection quantity measurement device may include: a rotational drive unit that rotates the collector or a travel direction of the electromagnetic wave to be measured while a line in a direction perpendicular to the travel direction of the electromagnetic wave to be measured is set as a rotational axis; and a linear drive unit that moves the collector or the travel direction of the electromagnetic wave to be measured in a direction perpendicular to the travel direction of the electromagnetic wave to be measured and the rotational axis, wherein the detection is carried out by the electromagnetic wave detector while the rotational drive unit and the linear drive unit are operating.

According to the first or second collection quantity measurement device of the present invention, a line segment which is an intersection portion of a line perpendicular to an extension direction of the first, second, and third hole portions and the collector may be contained in the reference area; and there may be a plurality of the travel directions of the electromagnetic wave to be measured, and one of them is fixed along the line segment.

According to the present invention, a collection quantity measurement method using a collection quantity measurement device having an electromagnetic wave output device that outputs an electromagnetic wave to be measured at a frequency equal to or higher than 0.01 [THz] and equal to or lower than 100 [THz] toward the first, second or third collector according to the present invention; and an electromagnetic wave detector that detects the electromagnetic wave to be measured which has transmitted through the collector; includes: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the third hole portion adjacent only to the third hole portion, and is on a side of the third hole portion with respect to a border between the third hole portion and the first or second hole portion; and the collection area is an area of the collector except for the reference area.

According to the present invention, a collection quantity measurement method using a collection quantity measurement device having an electromagnetic wave output device that outputs an electromagnetic wave to be measured at a frequency equal to or higher than 0.01 [THz] and equal to or lower than 100 [THz] toward the fourth collector according to the present invention; and an electromagnetic wave detector that detects the electromagnetic wave to be measured which has transmitted through the collector; includes: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the first hole portion or the second hole portion enclosed by the partition wall hard to pass; and the collection area is an area of the collector except for the reference area.

The present invention is a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward the first, second or third collector according to the present invention; and an electromagnetic wave detector that detects the electromagnetic wave to be measured which has transmitted through the collector; the collection quantity measurement process including: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the third hole portion adjacent only to the third hole portion, and is on a side of the third hole portion with respect to a border between the third hole portion and the first or second hole portion; and the collection area is an area of the collector except for the reference area.

The present invention is a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward the fourth collector according to the present invention; and an electromagnetic wave detector that detects the electromagnetic wave to be measured which has transmitted through the collector; the collection quantity measurement process including: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the first hole portion or the second hole portion enclosed by the partition wall hard to pass; and the collection area is an area of the collector except for the reference area.

The present invention is a computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward the first, second or third collector according to the present invention; and an electromagnetic wave detector that detects the electromagnetic wave to be measured which has transmitted through the collector; the collection quantity measurement process including: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the third hole portion adjacent only to the third hole portion, and is on a side of the third hole portion with respect to a border between the third hole portion and the first or second hole portion; and the collection area is an area of the collector except for the reference area.

The present invention is a computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward the fourth collector; and an electromagnetic wave detector that detects the electromagnetic wave to be measured which has transmitted through the collector; the collection quantity measurement process including: a reference value deriving step that derives, based on a result detected by the electromagnetic wave detector, any one of an absorption rate, a group delay, and a dispersion of the electromagnetic wave to be measured in a reference area; and a collection quantity deriving step that derives, based on the result detected by the electromagnetic wave detector and the result derived by the reference value deriving step, a weight or a density of the material present in an collection area, wherein: the reference area includes the first hole portion or the second hole portion enclosed by the partition wall hard to pass; and the collection area is an area of the collector except for the reference area.

BRIEF DESCRIPTION OF THE DRAWINGS

FIGS. 1(a) and 1(b) show a DPF 1 according to the first embodiment of the present invention, in which FIG. 1(a) is a front view, and FIG. 1(b) is a side view;

FIGS. 2(a) and 2(b) show the portion II of the DPF 1 shown in FIG. 1(a), in which FIG. 2(a) is a partial front view, and FIG. 2(b) is a side cross sectional view;

FIGS. 3(a) and 3(b) show the portion III of the DPF 1 shown in FIG. 1(a), in which FIG. 3(a) is a partial front view, and FIG. 3(b) is a side cross sectional view;

FIG. 4(a) and FIG. 4(b) are partial front view of the DPF 1, in which

FIG. 4(a) is a partial front view describing a reference area A0, and FIG. 4(b) is a partial front view describing a border B;

FIGS. 5(a) and 5(b) show a configuration of the collection quantity measurement device according to the first embodiment, in which FIG. 5(a) is a plan view and FIG. 5(b) is a partial front view;

FIGS. 6(a) and 6(b) show the portion II (refer to FIG. 1) of the DPF 1 according to a first variation of the first embodiment, in which FIG. 6(a) is a partial front view, and FIG. 6(b) is a side cross sectional view;

FIGS. 7(a) and 7(b) are front views of the DPF 1 according to a second variation of the first embodiment, in which FIG. 7(a) does not show a closing member 30, and FIG. 7(b) shows the closing member 30;

FIGS. 8(a) and 8(b) show the DPF 1 according to the second variation of the first embodiment, in which FIG. 8(a) is a partial front view without the closing member 30, and FIG. 8(b) is a side cross sectional view with the closing member 30;

FIGS. 9(a) and 9(b) show the DPF 1 according to the second embodiment of the present invention, in which FIG. 9(a) is a front view and FIG. 9(b) is a side view;

FIGS. 10(a) and 10(b) show a portion F of the DPF 1 shown in FIG. 9(a), in which FIG. 10(a) is a partial front view, and FIG. 10(b) is a side cross sectional view;

FIGS. 11(a) and 11(b) show the portion F (refer to FIG. 9) of the DPF 1 according to a first variation of the second embodiment, in which FIG. 11(a) is a partial front view, and FIG. 11(b) is a side cross sectional view;

FIG. 12 is a side cross sectional view of the portion F (refer to FIG. 9) of the DPF 1 according to a second variation of the second embodiment;

FIGS. 13(a) and 13(b) show the DPF 1 according to the third embodiment, in which FIG. 13(a) is a front view, and FIG. 13(b) is a side cross sectional view of a part XIII (refer to FIG. 13(b));

FIGS. 14(a) and 14(b) show the DPF 1 according to the fourth embodiment of the present invention, in which FIG. 14(a) is a front view and FIG. 14(b) is a side view;

FIGS. 16(a) and 16(b) show the DPF 1 according to the fifth embodiment of the present invention, in which FIG. 16(a) is a front view and FIG. 16(b) is a side view.

BEST MODE FOR CARRYING OUT THE INVENTION

Figure 1:
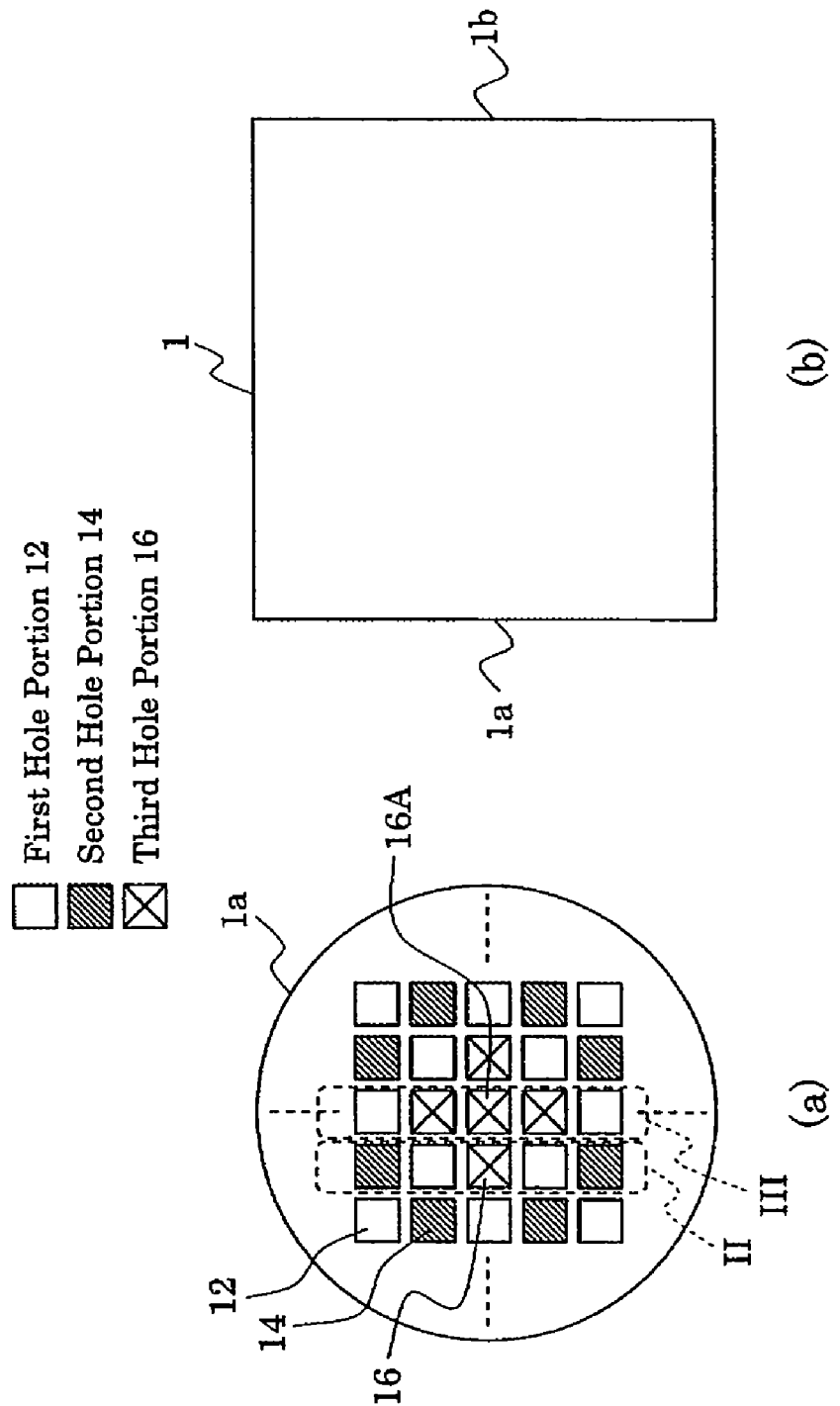

A description will now be given of embodiments of the present invention with reference to drawings.

First Embodiment

FIGS. 1(a) and 1(b) show a DPF 1 according to the first embodiment of the present invention, in which FIG. 1(a) is a front view, and FIG. 1(b) is a side view.

The diesel particulate filter (DPF) 1 according to the embodiment of the present invention receives an exhaust gas of a diesel engine or the like, and collects a particulate matter (PM) in the exhaust gas. For example, the DPF (collector) 1 is installed on an automobile equipped with a diesel engine. Moreover, for the DPF (collector) 1, a particulate matter attachment test is carried out.

The DPF (collector) 1 according to the first embodiment includes a first end surface 1a, and a second end surface 1b (refer to FIG. 1(b)). The first end surface 1a and second end surface 1b are circular (refer to FIG. 1(a)), and the DPF 1 itself is cylindrical. The DPF 1 receives the exhaust gas on the first end surface 1a, and discharges the exhaust gas on the second end surface 1b. The PM has been collected, and therefore, the exhaust gas discharged from the second end surface 1b is thus purified more than the exhaust gas received by the first end surface 1a.

The DPF (collector) 1 according to the first embodiment is further provided with first hole portions 12, second hole portions 14, and third hole portions 16. In FIG. 1(a), these hole portions are shown only in a vicinity of the center of the first end surface 1a. In the following section, the first hole portions 12, the second hole portions 14, and the third hole portions 16 may be generally referred to as "hole portions".

It should be noted that the third hole portions 16 are arranged approximately at the center of the first end surface 1*a* in FIG. 1(*a*). However, the third hole portions 16 may not be arranged approximately at the center of the first end surface 1*a*, and may be arranged in a portion close to the periphery of the first end surface 1*a*.

Referring to FIG. 1(*a*), the first hole portion 12 is placed at the upper left corner. The first hole portion 12 and the second hole portion 14 are adjacent to each other. The first hole portions 12 are not adjacent to each other, and the second hole portions 14 are not adjacent to each other. Moreover, the third hole portions 16 are adjacent to each other. On this occasion, a third hole portion 16A is adjacent only to the third hole portions 16 on upper, lower, left, and light sides of the third hole portion 16A. The third hole portion 16A is adjacent to neither the first hole portion 12 nor the second hole portion 14. The third hole portions 16 on the upper, lower, left, and right sides of the third hole portion 16A are adjacent to the third hole portion 16A as well as the first hole portions 12. It should be noted that the third hole portion 16A is located at the center of the first end surface 1*a*.

A single vertical column adjacent to the third hole portion 16A on the left side thereof is denoted by a portion II (containing five hole portions). Moreover, a single vertical column containing the third hole portion 16A is denoted by a portion III (containing five hole portions).

Figure 2:
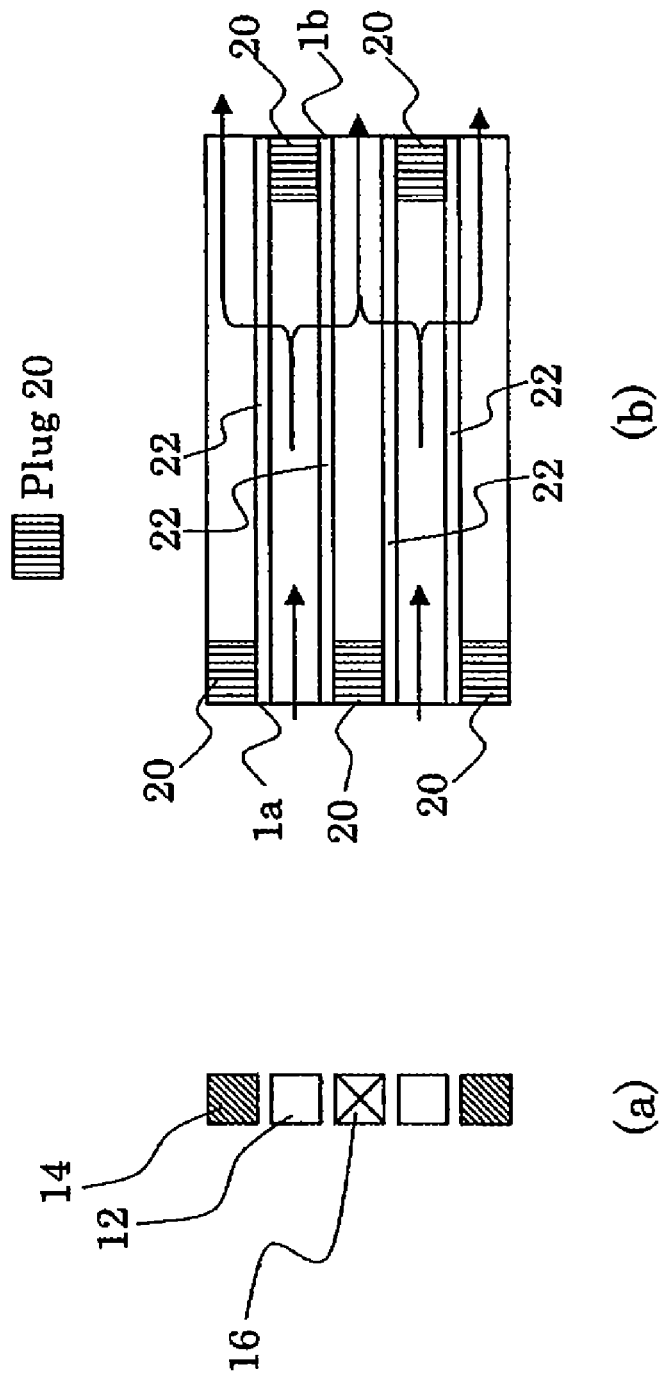
Figure 3:
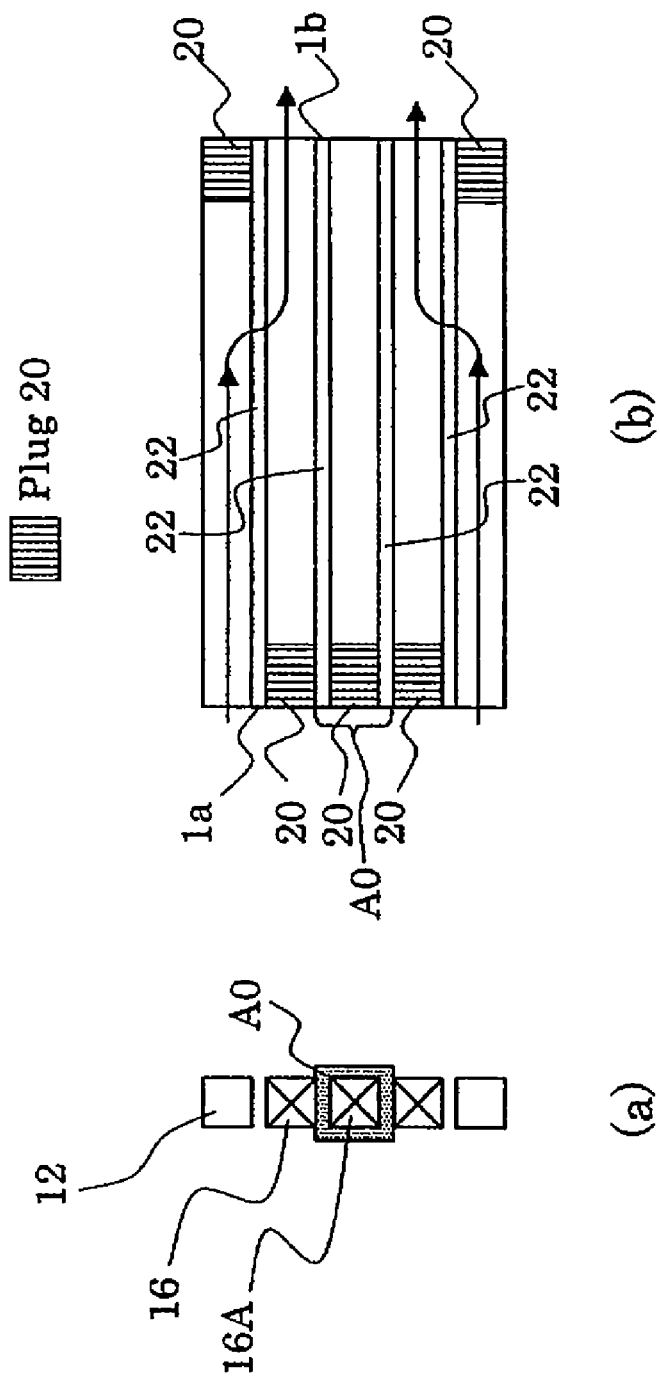

FIGS. 2(*a*) and 2(*b*) show the portion II of the DPF 1 shown in FIG. 1(*a*), in which FIG. 2(*a*) is a partial front view, and FIG. 2(*b*) is a side cross sectional view. FIGS. 3(*a*) and 3(*b*) show the portion III of the DPF 1 shown in FIG. 1(*a*), in which FIG. 3(*a*) is a partial front view, and FIG. 3(*b*) is a side cross sectional view. It should be noted that arrows represent flows of the exhaust gas in FIGS. 2(*b*) and 3(*b*).

Out of ends of the hole portions, an end on the first end surface 1*a* side is referred to as a first end, and an end on the second end surface 1*b* side is referred to as a second end. The first end is an end on the side for receiving the gas (exhaust gas). The second end is an end opposite to the first end.

The first hole portion 12 is open at the first end and is closed at the second end. The second hole portion 14 is closed at the first end, and is open at the second end. The third hole portion 16 is closed at the first end.

It should be noted that the second hole portion 14 and the third hole portion 16 have the closed first end in common. However, the second hole portion 14 and the third hole portion 16 are different from each other in that while the second hole portions 14 are not adjacent to each other, the third hole portions 16 are adjacent to each other.

A partition wall 22 is a wall partitioning between the first hole portion 12 and the second hole portion 14 adjacent to each other. The partition wall 22 is a porous ceramic such as cordierite. The PM in the exhaust gas passing through the partition wall 22 is collected by the partition wall 22.

Plugs 20 are disposed inside the first hole portion 12, the second hole portion 14, and the third hole portion 16. The plugs 20 close the first hole portion 12, the second hole portion 14, and the third hole portion 16.

FIG. 4(*a*) and FIG. 4(*b*) are partial front view of the DPF 1, in which FIG. 4(*a*) is a partial front view describing a reference area A0, and FIG. 4(*b*) is a partial front view describing a border B.

The reference area A0 includes third hole portions 16A adjacent only to the third hole portions 16. According to the first embodiment, the reference area A0 is an area constructed by the third hole portion 16A and partition walls 22 enclosing the third hole portion 16A.

A border line separating the third hole portions 16 from the first hole portions 12 and the second hole portions 14 is referred to as border B. The reference area A0 is inside the border B (on the side of the third hole portions 16).

A description will now be given of an operation of the first embodiment.

Referring to FIG. 2, the first end surface 1*a* of the DPF 1 receives the exhaust gas of the diesel engine. The exhaust gas flows into the inside of the first hole portions 12 which are second and fourth from the top out of the hole portions in the single vertical column in FIG. 2(*a*). The exhaust gas does not flow from the first ends (closed by the plugs 20) of the other hole portions.

The exhaust gas which has flown into the inside of the first hole portions 12 cannot flow through the second end (closed by the plug 20) of the first hole portions 12, and cannot flow out to the outside of the DPF 1. The partition walls 22 are made of the porous ceramic, and the exhaust gas flows through the partition walls 22 into the inside of the second hole portions 14 and the third hole portion 16. On this occasion, the PM in the exhaust gas cannot pass through the partition walls 22, and remains in the inside of the first hole portions 12. This is referred to as collection of the PM by the partition walls 22. The exhaust gas which has passed through the partition walls 22 has been purified as a result of the collection of the PM, and exits from the second ends of the second hole portions 14 and the third hole portion 16 to the outside of the DPF 1.

Referring to FIG. 3, the first end surface 1*a* of the DPF 1 receives the exhaust gas of the diesel engine. The exhaust gas flows into the inside of the first hole portions 12 which are first and fifth from the top out of the hole portions in a single vertical column in FIG. 2(*a*). The exhaust gas does not flow from the first ends (closed by the plugs 20) of the other hole portions.

The exhaust gas which has flown into the inside of the first hole portions 12 cannot flow through the second end (closed by the plug 20) of the first hole portions 12, and cannot flow out to the outside of the DPF 1. The partition walls 22 are made of the porous ceramic, and the exhaust gas flows through the partition walls 22 into the inside of the third hole portions 16 which are second and fourth from the top out of the hole portions in the single vertical column in FIG. 2(*a*). On this occasion, the PM in the exhaust gas cannot pass through the first and fourth partition walls 22 from the top in FIG. 2(*b*), and remains in the inside of the first hole portions 12.

The exhaust gas which has passed through the partition walls 22 has been purified as a result of the collection of the PM. On this occasion, both the second ends of the third hole portions 16 which are second and fourth from the top out of the hole portions in the single vertical column in FIG. 2(*a*) are open. Thus, the exhaust gas which has flown into the inside of the third hole portions 16 which are second and fourth from the top out of the hole portions in the single vertical column in FIG. 2(*a*) will not flow into the inside of the third hole portion 16A, but flows from the second ends of the third hole portions 16 which are second and fourth from the top out of the hole portions in the single vertical column in FIG. 2(*a*) to the outside of the DPF 1.

As a result, the PM in the exhaust gas will hardly attach to the reference area A0 constructed by the inside of the third hole portion 16A and the partition walls 22 enclosing the third hole portion 16A, and it is thus considered that a weight of the PM to be collected is almost zero.

A cross sectional area of the reference area A0 on a plane parallel to the first end surface 1*a* is extremely smaller than the area of the first end surface 1*a*. Therefore, a decrease in the quantity of the PM collected by the DPF 1 due to the presence of the reference area A0 is negligible.

The DPF 1 which has collected the PM in the exhaust gas is removed from the automobile or the device for the particulate matter attachment test. The quantity of the collected PM by the DPF 1 is then measured by a collection quantity measurement device.

Figure 5:
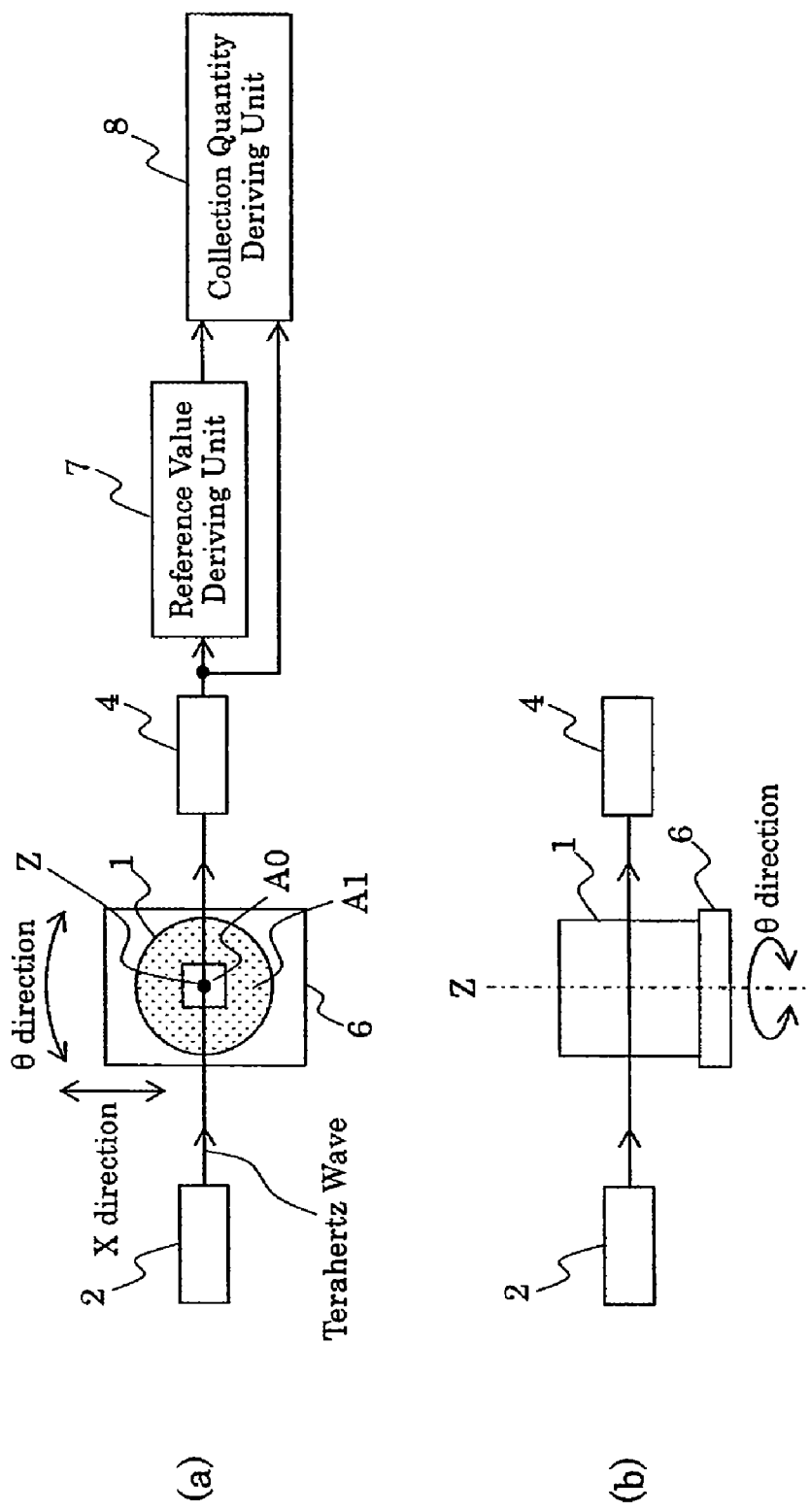

FIGS. 5(*a*) and 5(*b*) show a configuration of the collection quantity measurement device according to the first embodiment, in which FIG. 5(*a*) is a plan view and FIG. 5(*b*) is a partial front view. The collection quantity measurement device according to the first embodiment includes an electromagnetic wave output device 2, an electromagnetic wave detector 4, a scanning stage (rotational drive unit and a linear drive unit) 6, a reference value deriving unit 7, and a collection quantity deriving unit 8.

Referring to FIG. 5(*a*), an area other than the reference area A0 out of the DPF 1 is designated as a collection area A1. It should be noted that the DPF 1, the electromagnetic wave output device 2, the electromagnetic wave detector 4, and the scanning stage 6 are shown, and the reference value deriving unit 7 and the collection quantity deriving unit 8 are omitted in FIG. 5(*b*).

The electromagnetic wave output device 2 outputs an electromagnetic wave having a frequency equal to or more than 0.01 [THz] and equal to or less than 100 [THz] (hereinafter referred to as "electromagnetic wave to be measured") toward the DPF 1. The frequency of the electromagnetic wave to be measured output toward the DPF 1 includes a terahertz wave band (such as equal to or more than 0.03 [THz] and equal to or less than 10 [THz]). According to the embodiment of the present invention, it is assumed that a terahertz wave is employed as an example of the electromagnetic wave to be measured.

The terahertz wave output to the DPF 1 transmits through the DPF 1. The electromagnetic wave detector 4 detects the electromagnetic wave to be measured (such as a terahertz wave) which has transmitted through the DPF 1.

The scanning stage (a rotational drive unit and a linear drive unit) 6 rotates the DPF 1 while a line Z perpendicular to the travel direction of the electromagnetic wave to be measured is considered as a rotational axis (motion in a θ direction). It should be noted that the electromagnetic wave output device 2 and the electromagnetic wave detector 4 may be rotated while the line Z is set as a rotational axis (which corresponds to the rotation of the travel direction of the electromagnetic wave to be measured).

The scanning stage 6 moves the DPF 1 in a direction X (movement in the X direction) perpendicular to the travel direction of the electromagnetic wave to be measured and to the rotational axis Z. It should be noted that the electromagnetic wave output device 2 and the electromagnetic wave detector 4 may be moved in the X direction (which corresponds to the movement of the travel direction of the electromagnetic wave to be measured).

While the scanning stage (a rotational drive unit and a linear drive unit) 6 is in operation, the detection by the electromagnetic wave detector 4 is carried out.

The reference value deriving unit 7 derives, based on a result detected by the electromagnetic wave detector 4, any of an absorption rate, a group delay, and a dispersion of the terahertz wave in an inside of the reference area A0 (such as a cross section of the reference area A0 made on a plane perpendicular to the line Z). The absorption rate and the like of the terahertz wave in the reference area A0 can be derived by the widely-known computer tomography (CT).

The collection quantity deriving unit 8 derives, based on the result detected by the electromagnetic wave detector 4 and the result derived by the reference value deriving unit 7, a weight (unit thereof is [g], for example) or a density (unit thereof [g/l] (weight per liter), for example) of the PM present in the collection area A1.

A description will now be given of an example for causing the collection quantity deriving unit 8 to derive, based on the absorption rate of the terahertz wave in the reference area A0, the density of the PM present in the collection area A1.

The absorption rate of the terahertz wave when the density of the particulate matter is zero is denoted by $\alpha_0$, and an increase rate of the absorption rate of the terahertz wave with respect to the density of the particulate matter is denoted by $\beta$. Then, the density of the particulate matter is represented as $(\alpha - \alpha_0)/\beta$. It should be noted that $\beta$ is obtained in advance, and is recorded in the collection quantity deriving unit 8.

The PM is hardly collected in the reference area A0, and it can be considered that the density of the particulate matter is zero. Thus, the absorption rate of the terahertz wave in the reference area A0 derived by the reference value deriving unit 7 is considered as $\alpha_0$. Thus, the collection quantity deriving unit 8 can acquire $\alpha_0$ from the reference value deriving unit 7.

Moreover, the collection quantity deriving unit 8 derives a distribution of the absorption rate a of the terahertz wave in the collection area A1 from the result detected by the electromagnetic wave detector 4 by the widely-known CT.

Further, the collection quantity deriving unit 8 assigns a, $\alpha_0$, and 3 to $(\alpha - \alpha_0)/\beta$, thereby deriving a distribution of the density of the particulate matter.

It should be noted that the reference value deriving unit 7 and the collection quantity deriving unit 8 may be realize in the following manner. A computer is provided with a CPU, a hard disk, and a media (such as a floppy disk (registered trade mark) and a CD-ROM) reader, and the media reader is caused to read a medium recording a program realizing the reference value deriving unit 7 and the collection quantity deriving unit 8, thereby installing the program on the hard disk. This method may also realize the above-described functions.

According to the first embodiment, since the reference area A0 exists inside the DPF 1 to be measured, an error caused by a passage of time and an error caused by individual difference of the DPF 1 can be neglected. Thus, the characteristic values (such as the abruption rate) of the terahertz wave can be precisely measured when the density of the particulate matter is zero in the DPF 1 which collects the PM in the exhaust gas. As a result, the distribution of the density of the PM in the DPF 1 can be precisely derived.

It should be noted that the DPF 1 according to the first embodiment has the following two possible variations.

Figure 6:
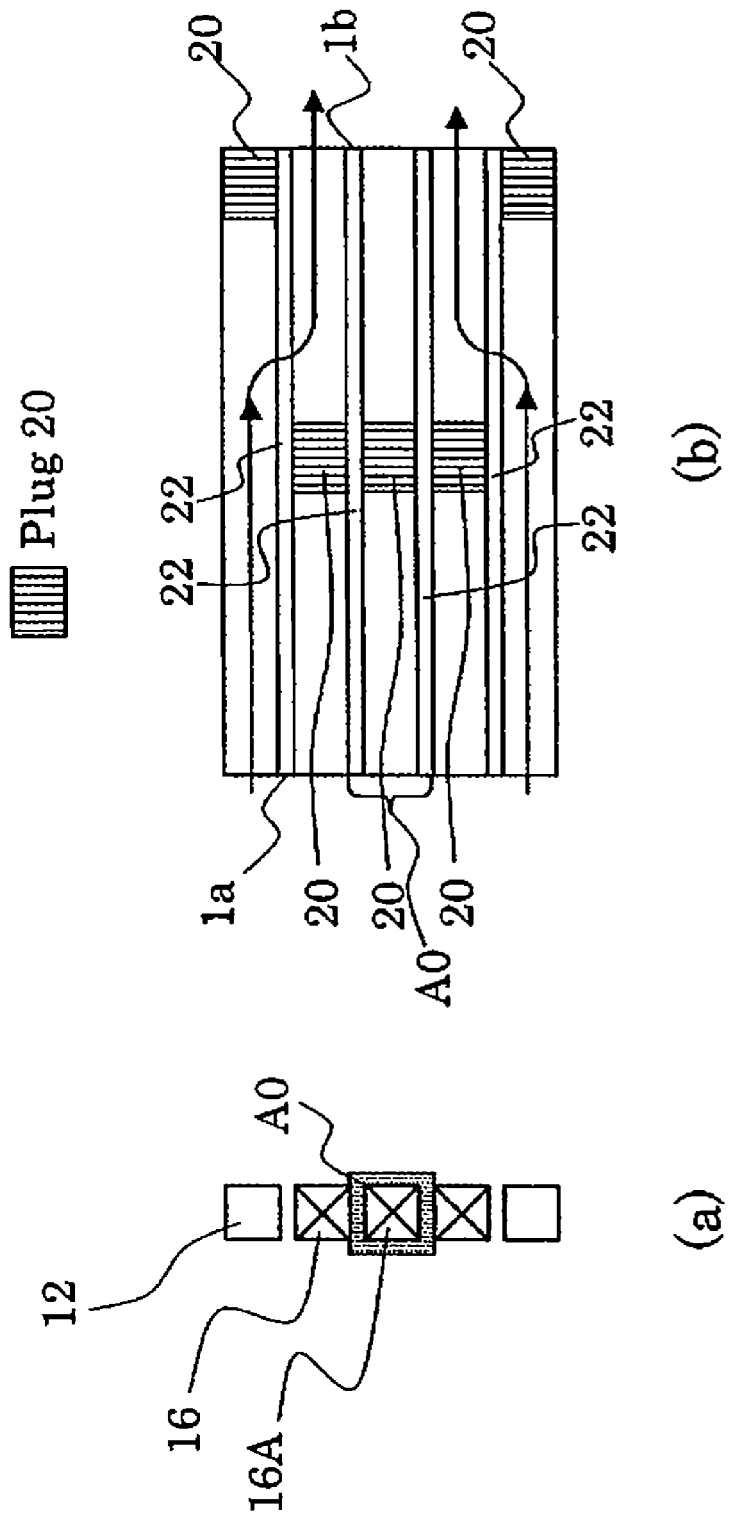

FIGS. 6(*a*) and 6(*b*) show the portion II (refer to FIG. 1) of the DPF 1 according to a first variation of the first embodiment, in which FIG. 6(*a*) is a partial front view, and FIG. 6(*b*) is a side cross sectional view. It should be noted that arrows represent flows of the exhaust gas in FIG. 6(*b*).

The third hole portion 16 is closed between the first end and the second end. The third hole portions are closed by the plugs 20 provided inside the third hole portions. For example, it is assumed that the plugs 20 are provided inside at the same distance from the first end of the third hole portions 16, and have the same shape.

The first variation is the same as the first embodiment except for the third hole portions 16, and a description thereof, therefore, is omitted.

FIGS. 7(a) and 7(b) are front views of the DPF 1 according to a second variation of the first embodiment, in which FIG. 7(a) does not show a closing member 30, and FIG. 7(b) shows the closing member 30.

Figure 8:
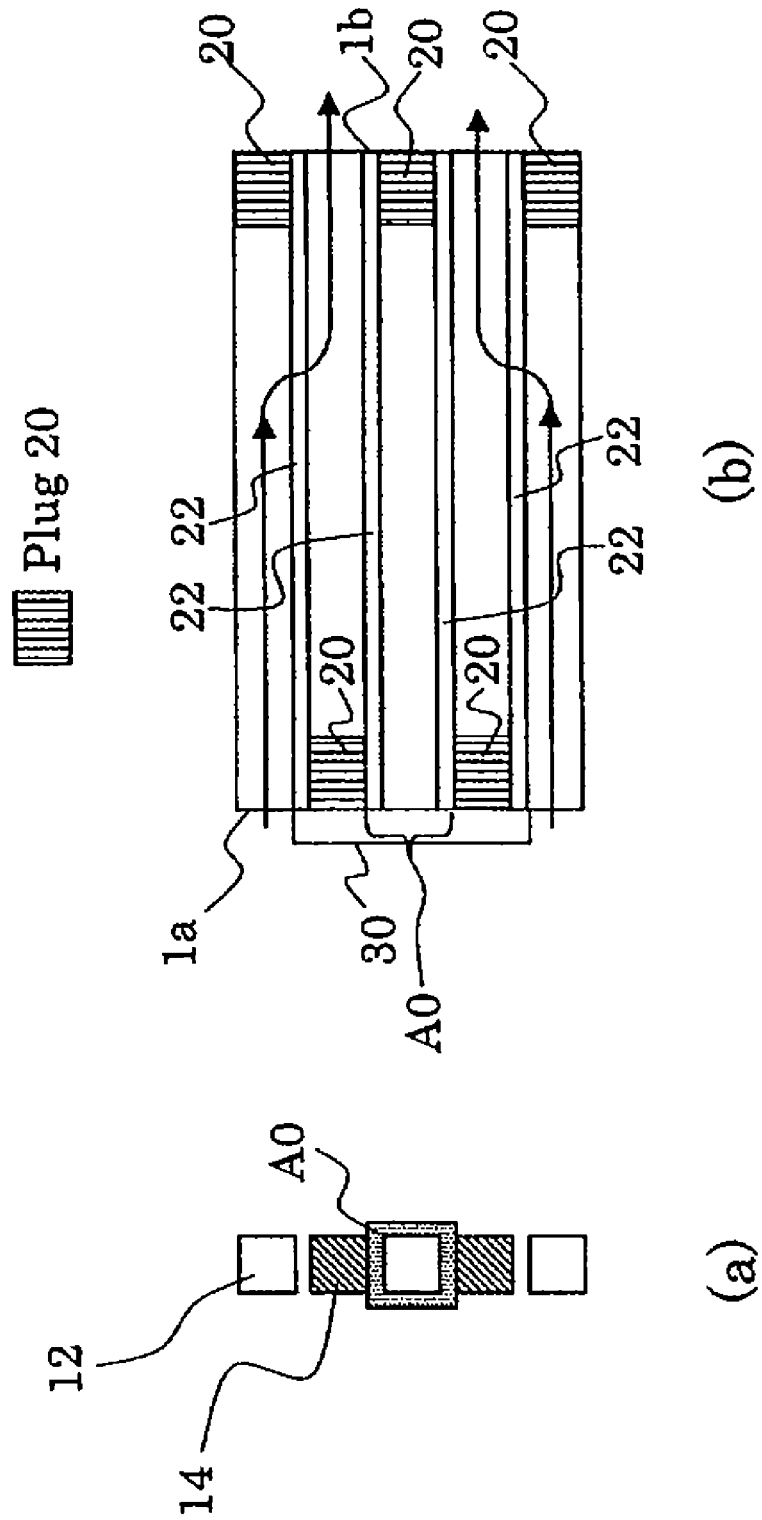

FIGS. 8(a) and 8(b) show the DPF 1 according to the second variation of the first embodiment, in which FIG. 8(a) is a partial front view without the closing member 30, and FIG. 8(b) is a side cross sectional view with the closing member 30. It should be noted that arrows represent flows of the exhaust gas in FIG. 8(b).

The DPF 1 according to the second variation of the first embodiment is provided with the closing member 30. The DPF 1 in the state without the closing member 30 does not include the third hole portions 16, and includes the first hole portions 12 and the second hole portions 14 as shown in FIG. 7(a). The DPF 1 according to the second variation of the first embodiment is obtained by placing the closing member 30 over the first hole portions 12 or the second hole portions 14 arranged as three vertical columns by three horizontal rows at the center of the DPF 1 as shown in FIG. 7(a). The closing member 30 is in contact with the end surface (first end surface 1a) of the first ends. As a result, the first hole portions 12 and the second hole portions 14 covered by the closing member 30 can serve as the third hole portions 16 (with the closed first end). It can be considered that the first ends of the third hole portions 16 are closed by the closing member 30.

The second variation is the same as the first embodiment except for the closing member 30, and a description thereof, therefore, is omitted.

Second Embodiment

The DPF 1 according to the second embodiment is obtained by exchanging the first hole portions 12 and the second hole portions 14 with each other in the DPF 1 according to the first embodiment. Moreover, the DPF 1 according to the second embodiment has the third hole portions 16 closed not at the first end, but at the second end.

Figure 9:
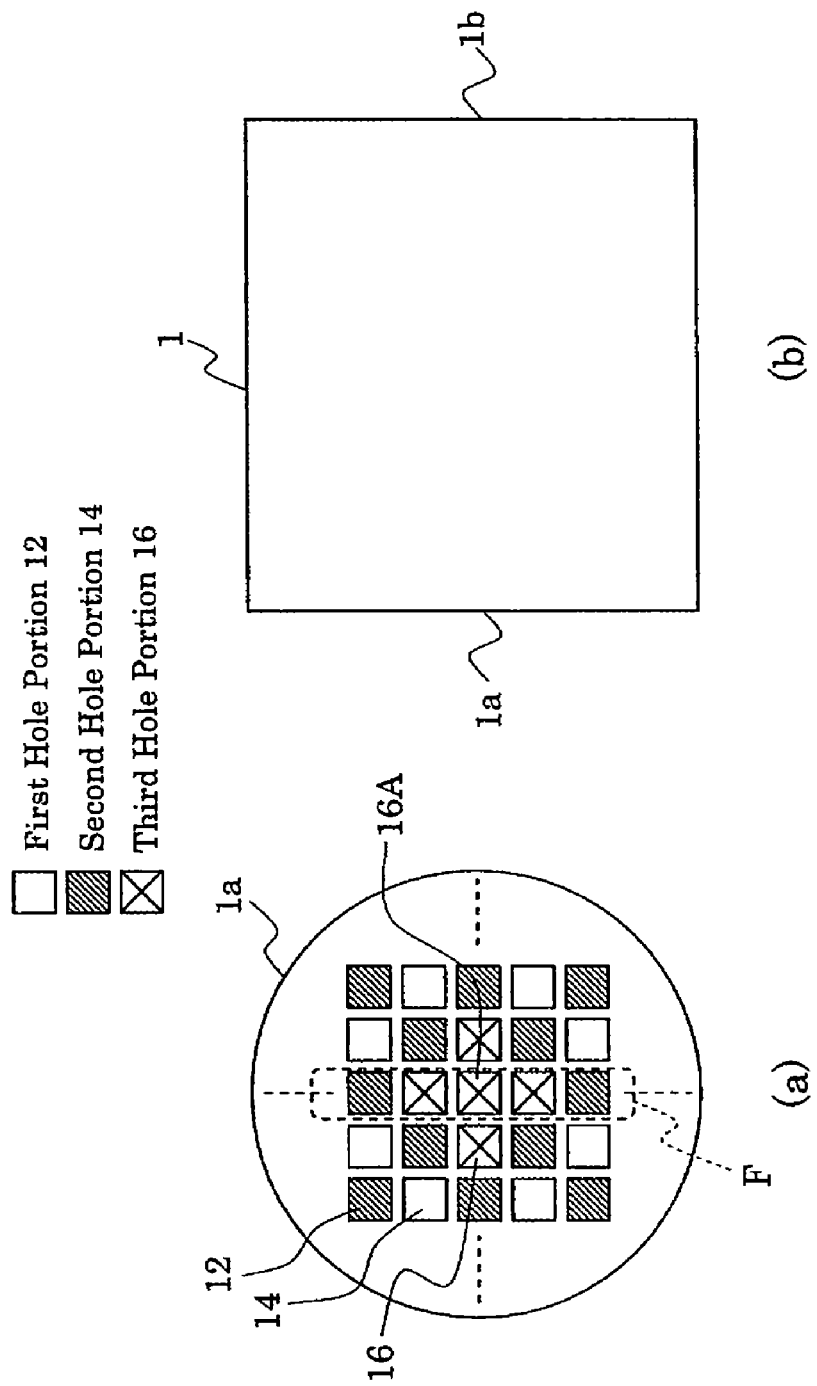

FIGS. 9(a) and 9(b) show the DPF 1 according to the second embodiment of the present invention, in which FIG. 9(a) is a front view and FIG. 9(b) is a side view. In the following section, the same components are denoted by the same numerals as of the DPF 1 according to the first embodiment, and will be explained in no more details.

The DPF (collector) 1 according to the second embodiment is provided with the first end surface 1a, the second end surface 1b, the first hole portions 12, the second hole portions 14, and the third hole portions 16.

It should be noted that the third hole portions 16 are arranged approximately at the center of the first end surface 1a in FIG. 9(a). However, the third hole portions 16 may not be arranged approximately at the center of the first end surface 1a, and may be arranged in a portion close to the periphery of the first end surface 1a.

The first end surface 1a and the second end surface 1b are the same as those of the first embodiment, and a description thereof, therefore, is omitted.

The first hole portions 12 and the second hole portions 14 are the same as those of the first embodiment except for the positions being mutually exchanged, and a description thereof, therefore, is omitted. Referring to FIG. 9(a), the second hole portion 14 is placed at the upper left corner.

Figure 10:
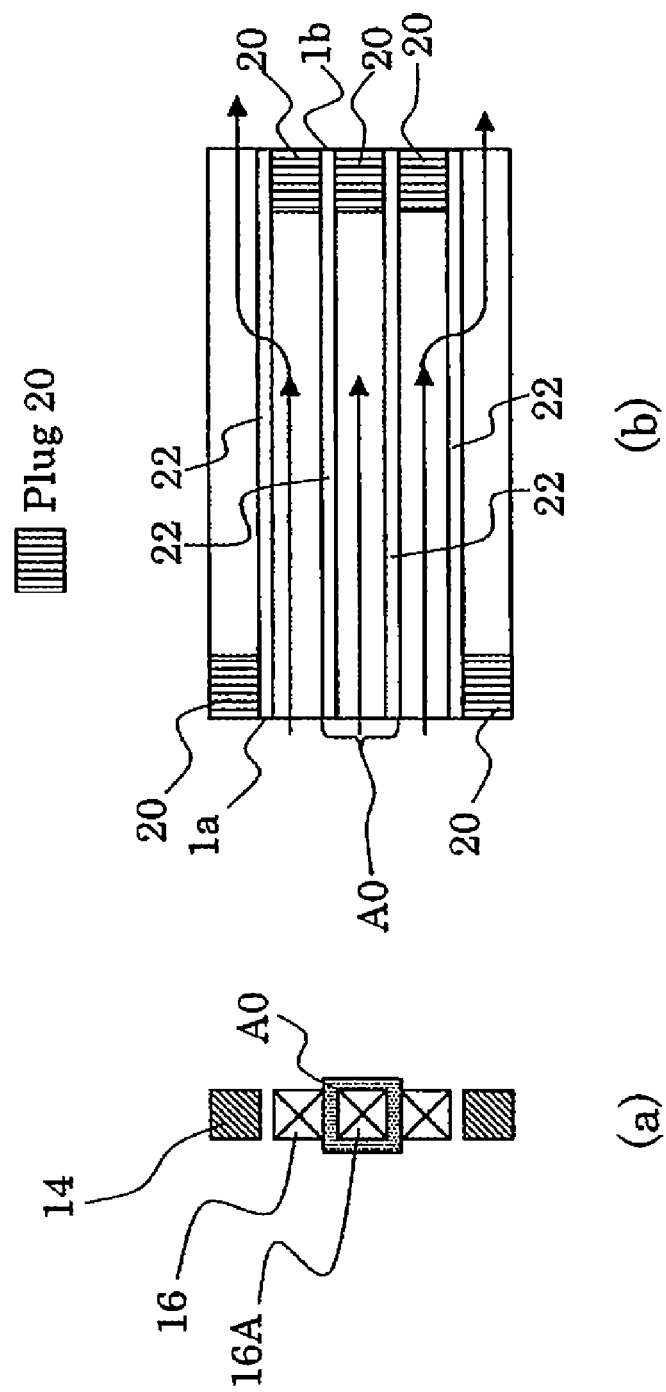

FIGS. 10(a) and 10(b) show a portion F of the DPF 1 shown in FIG. 9(a), in which FIG. 10(a) is a partial front view, and FIG. 10(b) is a side cross sectional view. It should be noted that arrows represent flows of the exhaust gas in FIG. 10(b).

The third hole portions 16 are closed at the second end (first end may be open). The third hole portion 16 is the same as that of the first embodiment except for this configuration, and a description thereof, therefore, is omitted. The plug 20, the partition wall 22, and the reference area A0 are the same as those of the first embodiment, and hence description thereof is omitted.

A description will now be given of an operation of the DPF 1 according to the second embodiment.

Referring to FIG. 10(b), the first end surface 1a of the DPF 1 receives the exhaust gas of the diesel engine. The exhaust gas flows into the inside of the third hole portions 16 which are second, third, and fourth from the top out of the hole portions in a single vertical column in FIG. 10(a). The exhaust gas will not flow from the first ends of the other hole portions.

The exhaust gas which has flown into the inside of the third hole portions 16 cannot flow through the second end (closed by the plug 20) of the third hole portions 16, and cannot flow out to the outside of the DPF 1. The partition walls 22 are made of the porous ceramic, and the exhaust gas flows through the partition walls 22 into the inside of the second hole portions 14 which are first and fifth from the top out of the hole portions in the single vertical column in FIG. 10(a). On this occasion, the PM in the exhaust gas cannot pass through the first and fourth partition walls 22 from the top in FIG. 10(b), and remains in the inside of the third hole portions 16.

The exhaust gas which has passed through the partition walls 22 has been purified as a result of the collection of the PM. On this occasion, both the second ends of the second hole portions 14 which are first and fifth from the top out of the hole portions in the single vertical column in FIG. 10(a) are open. Thus, the exhaust gas which has flown into the inside of the third hole portions 16 which are second and fourth from the top out of the hole portions in the single vertical column in FIG. 10(a) flows from the second ends of the third hole portions 16 to the outside of the DPF 1.

It should be noted that the pressure of the exhaust gas which has flown into the inside of the third hole portion 16A which is third from the top out of the hole portions in the single vertical column in FIG. 10(a) and the pressure of the exhaust gas which has flown into the inside of the third hole portions 16 which are second and fourth from the top out of the hole portions in the single vertical column in FIG. 10(a) are approximately the same. Thus, the exhaust gas which has flown into the inside of the third hole portion 16A hardly passes through the partition walls 22 and flows into the insides of the third hole portions 16 which are second and fourth from the top out of the hole portions in the single vertical column in FIG. 10(a).

As a result, the PM in the exhaust gas will hardly attach to the reference area A0 constructed by the inside of the third hole portion 16A and the partition walls 22 enclosing the third hole portion 16A, and it is thus considered that a weight of the PM to be collected is almost zero.

The extremely small size of the reference area A0 and the negligible decrease in the quantity of the PM collected by the DPF 1 due to the presence of the reference area A0 are also the same as those of the first embodiment.

The DPF 1 which has collected the PM in the exhaust gas is removed from the automobile or the device for the particulate matter attachment test. The quantity of the collected PM by the DPF 1 is then measured by a collection quantity measurement device. The collection quantity measurement device is the same as that of the first embodiment (refer to FIG. 5), and hence a description thereof is omitted. The configuration that the area other than the reference area A0 out of the DPF 1 is the collection area A1 is the same as the first embodiment.

According to the second embodiment, there are obtained the same effects as in the first embodiment.

It should be noted that the DPF 1 according to the second embodiment has the following two possible variations.

Figure 11:
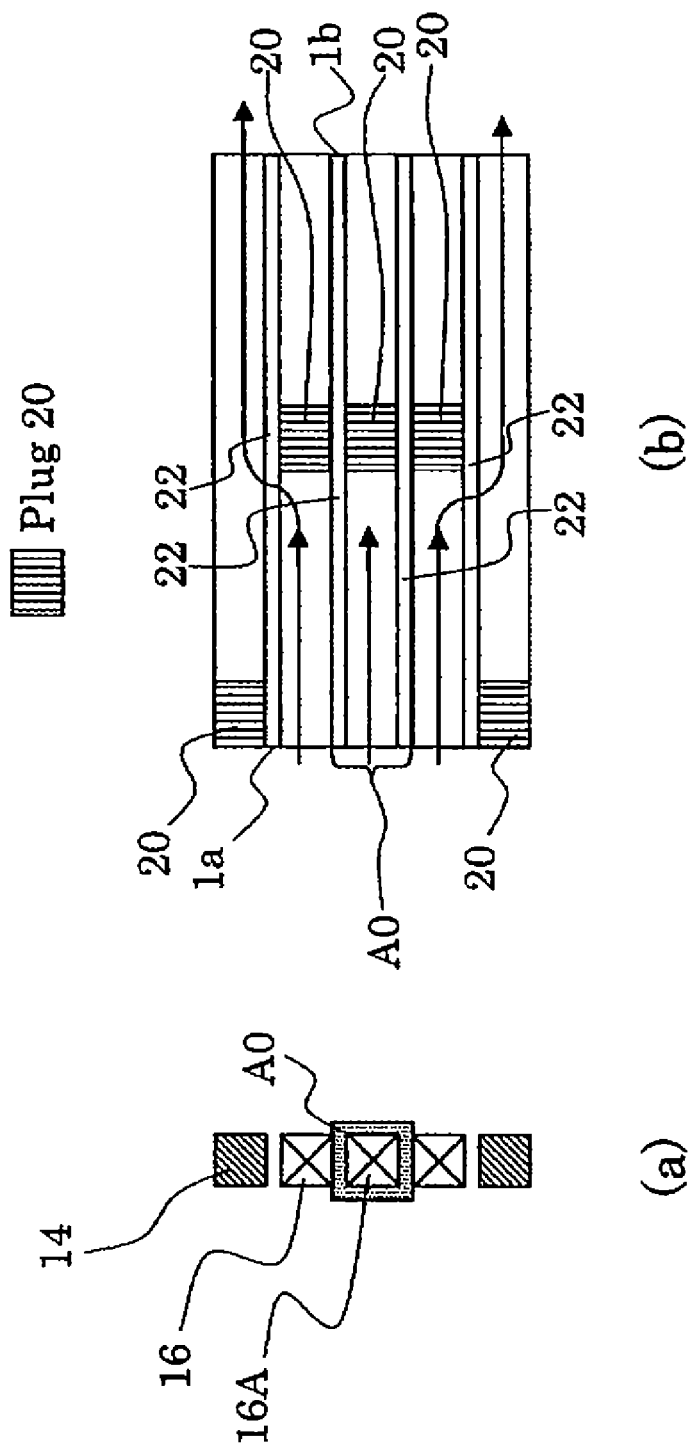

FIGS. 11(a) and 11(b) show the portion F (refer to FIG. 9) of the DPF 1 according to a first variation of the second embodiment, in which FIG. 11(a) is a partial front view, and FIG. 11(b) is a side cross sectional view. It should be noted that arrows represent flows of the exhaust gas in FIG. 11(b).

The third hole portion 16 is closed between the first end and the second end. The third hole portions are closed by the plugs 20 provided inside the third hole portions. For example, it is assumed that the plugs 20 are provided inside at the same distance from the first end of the third hole portions 16, and have the same shape.

The first variation is the same as the second embodiment except for the third hole portions 16, and a description thereof, therefore, is omitted.

FIG. 12 is a side cross sectional view of the portion F (refer to FIG. 9) of the DPF 1 according to a second variation of the second embodiment. It should be noted that arrows represent flows of the exhaust gas in FIG. 12.

The DPF 1 according to the second variation of the second embodiment is provided with the closing member 30. The second end surface 1b of the DPF 1 in the state without the closing member 30 does not include the third hole portions 16, and includes the first hole portions 12 and the second hole portions 14 as in FIG. 7(a). The DPF 1 according to the second variation of the second embodiment is obtained by placing the closing member 30 over the first hole portions 12 and the second hole portions 14 arranged as three vertical columns by three horizontal rows at the center of the second end surface 1b of the DPF 1 as in FIG. 7(b). The closing member 30 is in contact with the end surface (second end surface 1b) of the second ends. As a result, the first hole portions 12 and the second hole portions 14 covered by the closing member 30 can serve as the third hole portions 16 (with the closed second end). It can be considered that the second ends of the third hole portions 16 are closed by the closing member 30.

The second variation is the same as the second embodiment except for the closing member 30, and a description thereof, therefore, is omitted. It should be noted that the hole portion which is third from the top is closed by the closing member 30 at the second end as well as closed by the plug 20 at the first end, and the exhaust gas will not enter.

Third Embodiment

The DPF 1 according to the third embodiment is different from the DPF 1 according to the first embodiment in that the DPF 1 according to the third embodiment does not include the third hole portions 16, and includes partition walls easy to pass 32 and partition walls hard to pass 34.

Figure 13:
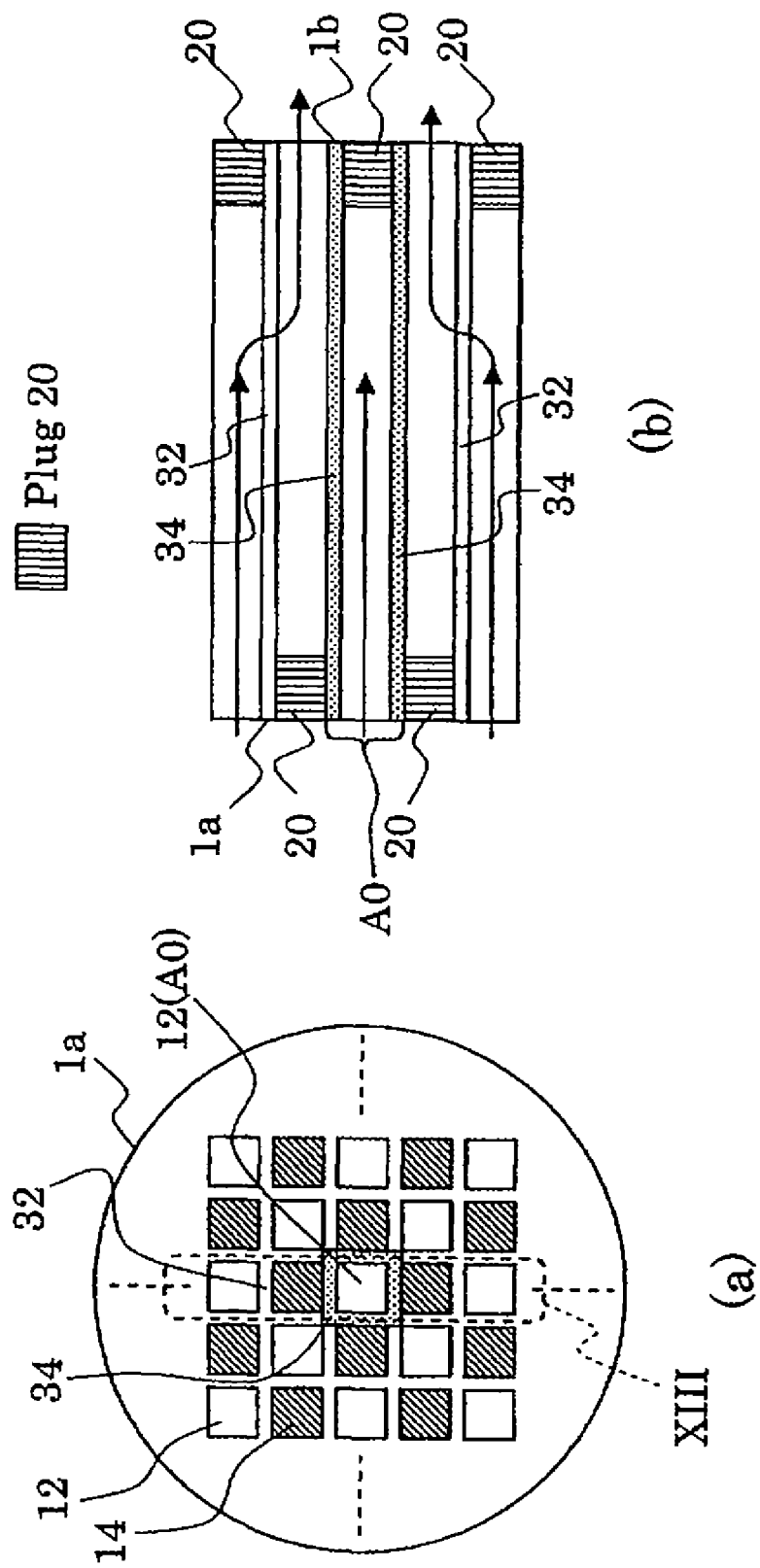

FIGS. 13(a) and 13(b) show the DPF 1 according to the third embodiment, in which FIG. 13(a) is a front view, and FIG. 13(b) is a side cross sectional view of a part XIII (refer to FIG. 13(b)). In the following section, the same components are denoted by the same numerals as of the DPF 1 according to the first embodiment, and will be explained in no more details. It should be noted that arrows represent flows of the exhaust gas in FIG. 13(b).

The DPF (collector) 1 according to the third embodiment is provided with the first end surface 1a, the second end surface 1b, the first hole portions 12, the second hole portions 14.

The first end surface 1a, the second end surface 1b, the first hole portion 12, and the second hole portion 14 are the same as those of the first embodiment, and a description thereof, therefore, is omitted.

A partition wall which partitions between the first hole portion 12 and the second hole portion 14, which are adjacent to each other, is the partition wall easy to pass 32 which is easy for the exhaust gas to pass through, or the partition wall hard to pass 34 which is hard for the exhaust gas to pass through.

For example, the porosity of the partition wall easy to pass 32 is set to higher than the porosity of the partition wall hard to pass 34. For example, the former one is 50%, and the latter one is 5%.

For example, the partition wall hard to pass 34 is made not to pass the exhaust gas. For example, if the partition wall hard to pass 34 is porous, a coating is applied to close the pores.

It is assumed that the reference area A0 contains the first hole portion or the second hole portion enclosed by the partition walls hard to pass 34. In the example shown in FIG. 13, the center first hole portion 12 is the reference area A0.

The configuration that the area other than the reference area A0 out of the DPF 1 is the collection area A1 is the same as the first embodiment.

A description will now be given of an operation of the DPF 1 according to the third embodiment.

Referring to FIG. 13(b), the first end surface 1a of the DPF 1 receives the exhaust gas of the diesel engine. The exhaust gas flows into the inside of the first hole portions 12 which are first and fifth from the top out of the hole portions in a single vertical column at the portion XIII in FIG. 13(a).

The exhaust gas which has flown into the inside of the first hole portions 12 cannot flow through the second end (closed by the plug 20) of the first hole portions 12, and cannot flow out to the outside of the DPF 1. The partition walls easy to pass 32 are made of the porous ceramic, and the exhaust gas flows through the partition walls easy to pass 32 into the inside of the second hole portions 14 which are second and fourth from the top out of the hole portions in the single vertical column at the portion XIII in FIG. 13(a). On this occasion, the PM in the exhaust gas cannot pass through the first and fourth partition walls easy to pass 32 from the top in FIG. 13(b), and remains in the inside of the first hole portions 12.

The exhaust gas which has passed through the partition walls easy to pass 32 has been purified as a result of the collection of the PM. On this occasion, both the second ends of the second hole portions 14 which are second and fourth from the top out of the hole portions in the single vertical column at the portion XIII in FIG. 13(a) are open. Thus, the exhaust gas which has flown into the inside of the second hole portions 14 which are second and fourth from the top out of the hole portions in the single vertical column at the portion XIII in FIG. 13(a) flows from the second ends of the second hole portions 14 to the outside of the DPF 1.

It is hard for the exhaust gas which has flown into the inside of the first hole portion 12 which is third from the top at the portion XIII in FIG. 13(a) to pass through the partition walls hard to pass 34, and the exhaust gas thus hardly flows into the inside of the other first hole portions 12.

As a result, the PM in the exhaust gas will hardly attach to the reference area A0 constructed by the first hole portion 12 which is third from the top at the portion XIII in FIG. 13(a), and it is thus considered that a weight of the PM to be collected is almost zero.

The extremely small size of the reference area A0 and the negligible decrease in the quantity of the PM collected by the DPF 1 due to the presence of the reference area A0 are also the same as those of the first embodiment.

The DPF 1 which has collected the PM in the exhaust gas is removed from the automobile or the device for the particulate matter attachment test. The quantity of the collected PM by the DPF 1 is then measured by a collection quantity measurement device. The collection quantity measurement device is the same as that of the first embodiment (refer to FIG. 5), and hence a description thereof is omitted.

According to the third embodiment, there are obtained the same effects as in the first embodiment.

Fourth Embodiment

The DPF 1 according to the fourth embodiment is different from the DPF 1 according to the first embodiment in the arrangement of the third hole portions 16. Moreover, the collection quantity measurement device for the DPF 1 according to the fourth embodiment is different from the collection quantity measurement device for the DPF 1 according to the first embodiment in that the collection quantity measurement device for the DPF 1 according to the fourth embodiment may not employ the CT.

Figure 14:
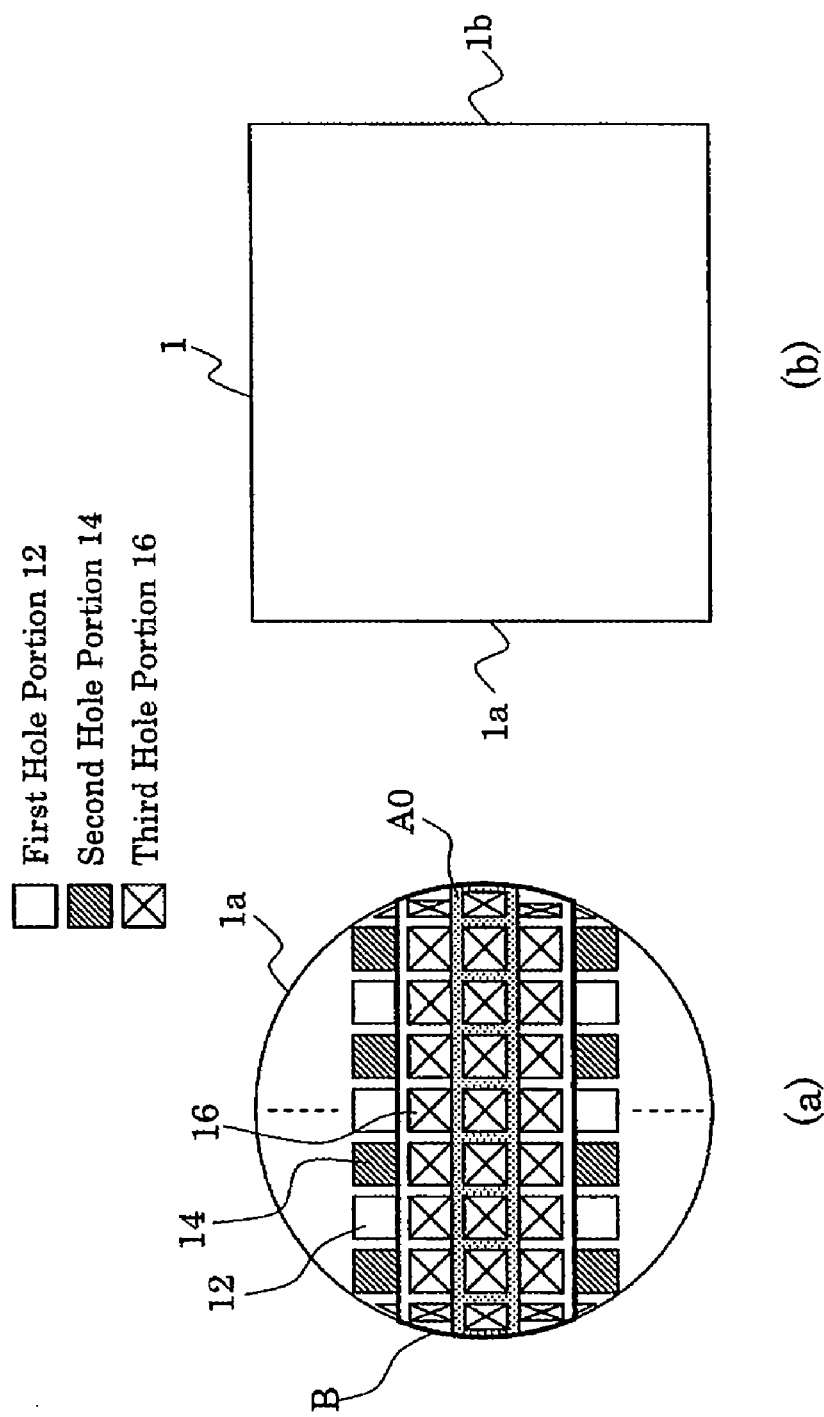

FIGS. 14(a) and 14(b) show the DPF 1 according to the fourth embodiment of the present invention, in which FIG. 14(a) is a front view and FIG. 14(b) is a side view. In the following section, the same components are denoted by the same numerals as of the DPF 1 according to the first embodiment, and will be explained in no more details.

The DPF (collector) 1 according to the fourth embodiment is provided with the first end surface 1a, the second end surface 1b, the first hole portions 12, the second hole portions 14, and the third hole portions 16.

The first end surface 1a, the second end surface 1b, the first hole portion 12, and the second hole portion 14 are the same as those of the first embodiment, and a description thereof, therefore, is omitted.

The third hole portions 16 are arranged as three horizontal rows at the center. In the three horizontal rows, neither the first hole portions 12 nor the second hole portions 14 are provided.

The reference area A0 includes the third hole portions 16 adjacent only to the third hole portions 16 (one horizontal row at the center). The reference area A0 is inside (on a side of the third hole portions 16) the border B which separates the third hole portion 16 from the first hole portion 12 or the second hole portion 14 (also includes a part of the outer periphery of the DPF 1).

For example, the reference area A0 includes the third hole portions 16 in the one horizontal row at the center, and the partition walls 22 enclosing the third hole portions 16 in the one horizontal row at the center.

A line segment PQ which is an intersection of a line perpendicular to a direction of the extension of the first hole portions 12, the second hole portions 14, and the third hole portions 16 (Z direction) and the DPF 1 (refer to FIG. 15) is inside the border B (on the side of the third hole portions 16).

The operation of the DPF 1 according to the fourth embodiment is the same as the operation of the DPF 1 according to the first embodiment, and hence a description thereof is omitted.

Then, the collection quantity of the PM of the DPF 1 which has collected the PM in the exhaust gas is measured by the collection quantity measurement device. The collection quantity measurement device may be the collection quantity measurement device according to the first embodiment which employs the CT, or may be other devices.

Figure 15:
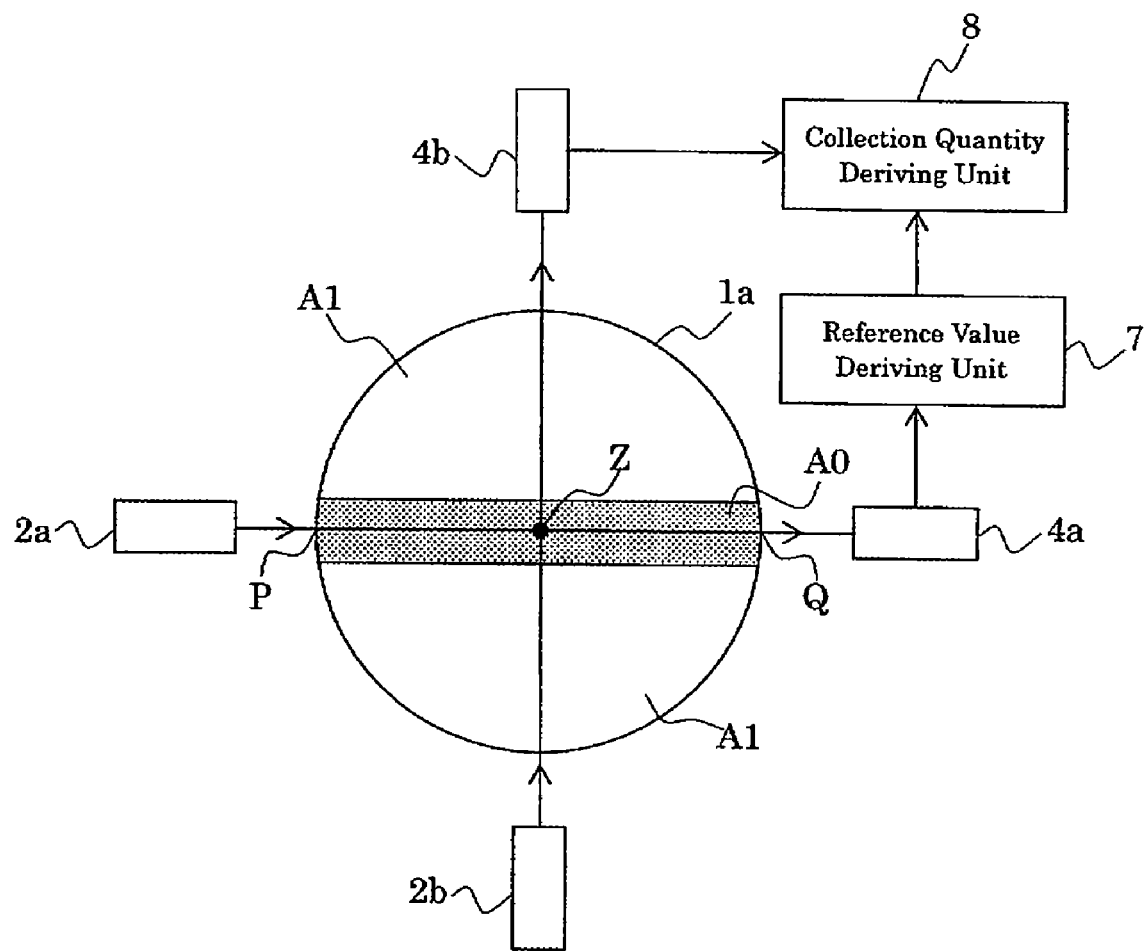
FIG. 15 is a plan view showing a configuration of the collection quantity measurement device according to the fourth embodiment.

FIG. 15 is a plan view showing a configuration of the collection quantity measurement device according to the fourth embodiment. The collection quantity measurement device according to the fourth embodiment includes electromagnetic wave output devices 2a and 2b, electromagnetic wave detectors 4a and 4b, the reference value deriving unit 7, and the collection quantity deriving unit 8.

The electromagnetic wave output devices 2a and 2b, and the electromagnetic wave detectors 4a and 4b are approximately the same as those of the first embodiment.

It should be noted that the terahertz wave output from the electromagnetic wave output device 2a toward the DPF 1 transmits through the DPF 1, and is detected by the electromagnetic wave detector 4a. Moreover, the terahertz wave output from the electromagnetic wave output device 2b toward the DPF 1 transmits through the DPF 1, and is detected by the electromagnetic wave detector 4b.

The reference area A0 contains the line segment PQ. An area other than the reference area A0 out of the DPF 1 is designated as the collection area A1.

The travel direction of the terahertz wave traveling from the electromagnetic wave output device 2a to the electromagnetic wave detector 4a is fixed on the line segment PQ. The travel direction of the terahertz wave traveling from the electromagnetic wave output device 2b to the electromagnetic wave detector 4b is perpendicular to the line segment PQ. In this way, there are the two types of the travel direction of the terahertz wave. The travel directions of the terahertz wave are fixed with respect to the DPF 1.

It should be noted that the DPF 1 itself is cylindrical. The axis Z which is the center of rotation of the DPF 1 and the line segment PQ intersect with each other. In other words, the line segment PQ overlaps the diameter of an (circular) cross section of the DPF 1 made on a plane perpendicular to the line Z.

The reference value deriving unit 7 derives, based on a result detected by the electromagnetic wave detector 4a, any of the absorption rate, the group delay, and the dispersion of the terahertz wave in the inside of the reference area A0 (such as a cross section of the reference area A0 made on a plane perpendicular to the line Z).

The absorption rate of the terahertz wave in the reference area A0 can be obtained without particularly employing the CT. For example, the absorption rate of the terahertz wave in the reference area A0 is obtained as 1−(the optical power of the terahertz wave detected by the electromagnetic wave detector 4a)/(the optical power of the terahertz wave output from the electromagnetic wave output device 2a).

The collection quantity deriving unit 8 derives, based on the result detected by the electromagnetic wave detector 4b and the result derived by the reference value deriving unit 7, the mass (unit thereof is [g], for example) or the density (unit thereof [g/l] (weight per liter), for example) of the PM present in the collection area A1.

If it is assumed that the density of the PM present in the collection area A1 and the absorption rate of the terahertz wave are the same at any portion in the collection area A1, the density of the particulate matter (PM) present in the collection area A1 can be derived as in the first embodiment.

The collection quantity measurement device according to the fourth embodiment does not require the scanning stage 6, is thus reduced in size, and can be installed on an automobile. Therefore, the measurement by the collection quantity measurement device can be carried out without removing the DPF 1 from the automobile.

Fifth Embodiment

The DPF 1 according to the fifth embodiment is different from the DPF 1 according to the third embodiment in the arrangement of the partition walls hard to pass 34. Moreover, the collection quantity measurement device for the DPF 1 according to the fifth embodiment is different from the collection quantity measurement device for the DPF 1 according to the third embodiment in necessity of the employment of the CT, and may not employ the CT.

Figure 16:
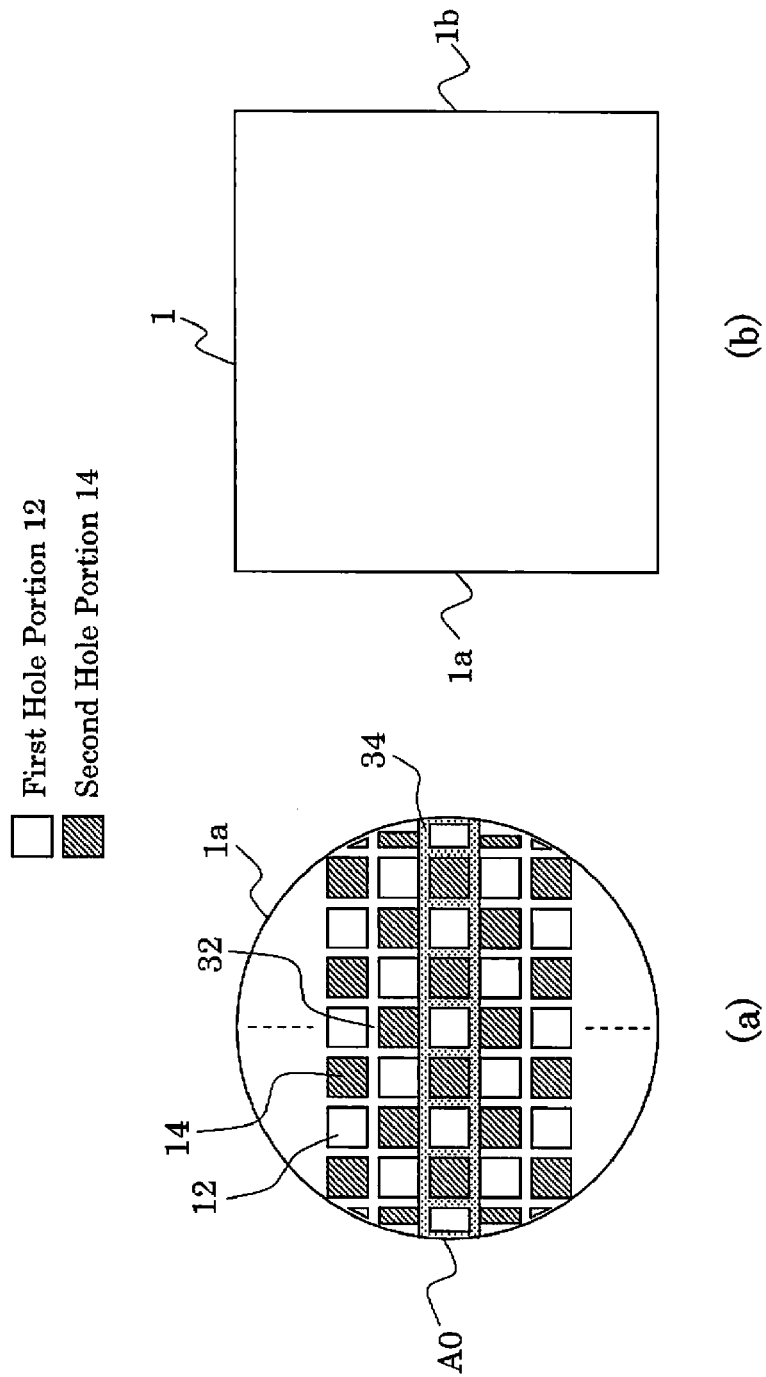

FIGS. 16(a) and 16(b) show the DPF 1 according to the fifth embodiment of the present invention, in which FIG. 16(a) is a front view and FIG. 16(b) is a side view. In the following section, the same components are denoted by the same numerals as of the third embodiment of the DPF 1, and will be explained in no more details.

The DPF (collector) 1 according to the fifth embodiment is provided with the first end surface 1a, the second end surface 1b, the first hole portions 12, and the second hole portions 14.

The first end surface 1a, the second end surface 1b, the first hole portion 12, and the second hole portion 14 are the same as those of the third embodiment, and a description thereof, therefore, is omitted.

The partition wall easy to pass 32 and the partition wall hard to pass 34 are also the same as those of the third embodiment, and a description thereof, therefore, is omitted. However, the first hole portions 12 and the second hole portions 14 in one horizontal row at the center is enclosed by the partition walls hard to pass 34. Partition walls at the other portions are partition walls easy to pass 32.

The line segment PQ which is the intersection of the line perpendicular to the direction of the extension of the first hole portions 12, the second hole portions 14, and the third hole portions 16 (Z direction) and the DPF 1 (refer to FIG. 15) passes through the first hole portions 12 and the second hole portions 14 in the one horizontal row at the center out of the first hole portions 12 and the second hole portions 14.

The first hole portions 12 and the second hole portions 14 in the one horizontal row at the center are the first hole portions 12 adjacent to the second hole portions 14 only via the partition walls hard to pass 34, and the second hole portions 14 adjacent to the first hole portions 12 only via the partition walls hard to pass 34.

The first hole portions 12 and the second hole portions 14 in the one horizontal row at the center are neither the first hole portions 12 adjacent to the second hole portions 14 via the partition walls easy to pass 32, nor the second hole portions 14 adjacent to the first hole portions 12 via the partition walls easy to pass 32.

The reference area A0 contains the first hole portions 12 or the second hole portions 14 enclosed by the partition walls hard to pass 34. The reference area A0 is constructed by the first hole portions 12 or the second hole portions 14 arranged in the one horizontal row at the center, and the partition walls hard to pass 34.

The operation of the DPF 1 according to the fifth embodiment is the same as the operation of the DPF 1 according to the third embodiment, and hence a description thereof is omitted.

Then, the collection quantity of the PM of the DPF 1 which has collected the PM in the exhaust gas is measured by the collection quantity measurement device. The collection quantity measurement device may be the same as the collection quantity measurement device employing the CT according to the first embodiment, or may be the same as the collection quantity measurement device according to the fourth embodiment (refer to FIG. 15).

The collection quantity measurement device according to the fifth embodiment can be reduced in size as the collection quantity measurement device according to the fourth embodiment.

The invention claimed is:

1. A collector which receives a gas, and collects a material in the gas, comprising:
    a first hole portion that is open at a first end on a side for receiving the gas, and is closed at a second end on a side opposite to the first end; and
    a second hole portion that is closed at the first end, and is open at the second end, wherein:
    the first hole portion and the second hole portion are adjacent to each other;
    a partition wall which partitions between the first hole portion and the second hole portion adjacent to each other is an partition wall which is easy for the gas to pass through or a partition wall which is hard for the gas to pass through; and
    the material in the gas is collected by the partition wall when the gas passes through the partition wall,
    wherein a line segment, which is an intersection portion of a line perpendicular to an extension direction of the first and second hole portions and the collector, passes through the first hole portion adjacent to the second hole portion via only the partition wall which is hard for the gas to pass through and the second hole portion adjacent to the first hole portion via only the partition wall which is hard for the gas to pass through, and does not pass through the first hole portion adjacent to the second hole portion via the partition wall which is easy for the gas to pass through and the second hole portion adjacent to the first hole portion via the partition wall which is easy for the gas to pass through.

2. The collector according to claim 1, wherein the partition wall which is easy for the gas to pass through is higher in porosity than the partition wall which is hard for the gas to pass through.

3. The collector according to claim 1, wherein the partition wall which is hard for the gas to pass through does not pass the gas.

4. The collector according to claim 1, wherein:
    the collector is cylindrical; and
    the line intersects with an axis of the center of rotation of the collector.

5. A collection quantity measurement device comprising:
    an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
    a first hole portion that is open at a first end on a side for receiving the gas, and is closed at a second end on a side opposite to the first end;
    a second hole portion that is closed at the first end, and is open at the second end; and
    a third hole portion that is closed at the first end, wherein:
    the first hole portion and the second hole portion are adjacent to each other;
    the third hole portions are adjacent to each other; and
    the material in the gas passing through a partition wall partitioning the first hole portion and the second hole portion adjacent to each other is collected by the partition wall;

wherein the collection quantity measurement device further comprises:
an electromagnetic wave detector that detects the electromagnetic wave to be measured which has transmitted through the collector;
a reference value deriving unit that derives, based on a result detected by the electromagnetic wave detector, any one of an absorption rate, a group delay, and a dispersion of the electromagnetic wave to be measured in a reference area; and
a collection quantity deriving unit that derives, based on the result detected by the electromagnetic wave detector and the result derived by the reference value deriving unit, a weight or a density of the material present in an collection area, wherein:
the reference area includes the third hole portion adjacent only to the third hole portion, and is on a side of the third hole portion with respect to a border between the third hole portion and the first or second hole portion; and
the collection area is an area of the collector except for the reference area.

6. The collection quantity measurement device according to claim 5, comprising:
a rotational drive unit that rotates the collector or a travel direction of the electromagnetic wave to be measured while a line in a direction perpendicular to the travel direction of the electromagnetic wave to be measured is set as a rotational axis; and
a linear drive unit that moves the collector or the travel direction of the electromagnetic wave to be measured in a direction perpendicular to the travel direction of the electromagnetic wave to be measured and the rotational axis,
wherein the detection is carried out by the electromagnetic wave detector while the rotational drive unit and the linear drive unit are operating.

7. The collection quantity measurement device according to claim 5, wherein:
a line segment which is an intersection portion of a line perpendicular to an extension direction of the first, second, and third hole portions and the collector is contained in the reference area; and
there are a plurality of the travel directions of the electromagnetic wave to be measured, and one of them is fixed along the line segment.

8. A collection quantity measurement device comprising:
an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
a first hole portion that is open at a first end on a side for receiving the gas, and is closed_at a second end on a side opposite to the first end; and
a second hole portion that is closed at the first end, and is open at the second end, wherein:
the first hole portion and the second hole portion are adjacent to each other;
a partition wall which partitions between the first hole portion and the second hole portion adjacent to each other is a partition wall which is easy for the gas to pass through or a partition wall which is hard for the gas to pass through; and
the material in the gas is collected by the partition wall when the gas passes through the partition wall;

wherein the collection quantity measurement device further comprises:
an electromagnetic wave detector that detects the electromagnetic wave to be measured which has transmitted through the collector;
a reference value deriving unit that derives, based on a result detected by the electromagnetic wave detector, any one of an absorption rate, a group delay, and a dispersion of the electromagnetic wave to be measured in a reference area; and
a collection quantity deriving unit that derives, based on the result detected by the electromagnetic wave detector and the result derived by the reference value deriving unit, a weight or a density of the material present in an collection area, wherein:
the reference area includes the first hole portion or the second hole portion enclosed by the partition wall which is hard for the gas to pass through; and
the collection area is an area of the collector coexisting with, but separate from, the reference area.

9. The collection quantity measurement device according to claim 8, comprising:
a rotational drive unit that rotates the collector or a travel direction of the electromagnetic wave to be measured while a line in a direction perpendicular to the travel direction of the electromagnetic wave to be measured is set as a rotational axis; and
a linear drive unit that moves the collector or the travel direction of the electromagnetic wave to be measured in a direction perpendicular to the travel direction of the electromagnetic wave to be measured and the rotational axis,
wherein the detection is carried out by the electromagnetic wave detector while the rotational drive unit and the linear drive unit are operating.

10. The collection quantity measurement device according to claim 8, wherein:
a line segment which is an intersection portion of a line perpendicular to an extension direction of the first, second, and third hole portions and the collector is contained in the reference area; and
there are a plurality of the travel directions of the electromagnetic wave to be measured, and one of them is fixed along the line segment.

11. A collection quantity measurement method using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
a first hole portion that is open at a first end on a side for receiving the gas, and is closed at a second end on a side opposite to the first end;
a second hole portion that is closed at the first end, and is open at the second end; and
a third hole portion that is closed at the first end, wherein:
the first hole portion and the second hole portion are adjacent to each other;
the third hole portions are adjacent to each other; and
the material in the gas passing through a partition wall partitioning the first hole portion and the second hole portion adjacent to each other is collected by the partition wall;
wherein the collection quantity measurement device further comprises an electromagnetic wave detector that detects the electromagnetic wave to be measured which has transmitted through the collector;

wherein the collection quantity measurement method comprises:

deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

12. A collection quantity measurement method using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed at a second end on a side opposite to the first end; and a second hole portion that is closed at the first end, and is open at the second end, wherein:

the first hole portion and the second hole portion are adjacent to each other;

a partition wall which partitions between the first hole portion and the second hole portion adjacent to each other is a partition wall which is easy for the gas to pass through or a partition wall which is hard for the gas to pass through; and the material in the gas is collected by the partition wall when the gas passes through the partition wall;

wherein the collection quantity measurement device further comprises an electromagnetic wave detector that detects the electromagnetic wave to be measured which has transmitted through the collector;

wherein said collection quantity measurement process comprises:

deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the first hole portion or the second hole portion enclosed by the partition wall which is hard for the gas to pass through; and the collection area is an area of the collector coexisting with, but separate from, the reference area.

13. A computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed at a second end on a side opposite to the first end;

a second hole portion that is closed at the first end, and is open at the second end; and a third hole portion that is closed at the first end, wherein:

the first hole portion and the second hole portion are adjacent to each other;

the third hole portions are adjacent to each other; and the material in the gas passing through a partition wall partitioning the first hole_portion and the second hole portion adjacent to each other is collected by the partition wall;

wherein the collection quantity measurement device further comprises an electromagnetic wave detector that detects the electromagnetic wave to be measured which has transmitted through the collector;

wherein said collection quantity measurement process comprises:

deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

14. A computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed_at a second end on a side opposite to the first end; and a second hole portion that is closed at the first end, and is open at the second end, wherein:

the first hole portion and the second hole portion are adjacent to each other;

a partition wall which partitions between the first hole portion and the second hole portion adjacent to each other is a partition wall which is easy for the gas to pass through or a partition wall which is hard for the gas to pass through; and the material in the gas is collected by the partition wall when the gas passes through the partition wall;

wherein the collection quantity measurement device further comprises an electromagnetic wave detector that detects the electromagnetic wave to be measured which has transmitted through the collector;

wherein said collection quantity measurement process comprises:

deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the first hole portion or the second hole portion enclosed by the partition wall which is hard for the gas to pass through; and the collection area is an area of the collector coexisting with, but separate from, the reference area.

15. A collection quantity measurement device comprising:
an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed at a second end on a side opposite to the first end;

a second hole portion that is closed at the first end, and is open at the second end; and a third hole portion that is closed at the second end, wherein:

the first hole portion and the second hole portion are adjacent to each other;

the third hole portions are adjacent to each other; and the material in the gas passing through a partition wall partitioning the first hole portion and the second hole portion adjacent to each other is collected by the partition wall;

wherein the collection quantity measurement device further comprises:

an electromagnetic wave detector that detects the electromagnetic wave to be measured which has transmitted through the collector;

a reference value deriving unit that derives, based on a result detected by the electromagnetic wave detector, any one of an absorption rate, a group delay, and a dispersion of the electromagnetic wave to be measured in a reference area; and a collection quantity deriving unit that derives, based on the result detected by the electromagnetic wave detector and the result derived by the reference value deriving unit, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

16. The collection quantity measurement device according to claim 15, comprising:

a rotational drive unit that rotates the collector or a travel direction of the electromagnetic wave to be measured while a line in a direction perpendicular to the travel direction of the electromagnetic wave to be measured is set as a rotational axis; and a linear drive unit that moves the collector or the travel direction of the electromagnetic wave to be measured in a direction perpendicular to the travel direction of the electromagnetic wave to be measured and the rotational axis, wherein the detection is carried out by the electromagnetic wave detector while the rotational drive unit and the linear drive unit are operating.

17. The collection quantity measurement device according to claim 15, wherein:

a line segment which is an intersection portion of a line perpendicular to an extension direction of the first, second, and third hole portions and the collector is contained in the reference area; and there are a plurality of the travel directions of the electromagnetic wave to be measured, and one of them is fixed along the line segment.

18. A collection quantity measurement device comprising:
an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed at a second end on a side opposite to the first end;

a second hole portion that is closed at the first end, and is open at the second end; and a third hole portion that is closed between the first end and the second end, wherein:

the first hole portion and the second hole portion are adjacent to each other;

the third hole portions are adjacent to each other; and the material in the gas passing through a partition wall partitioning the first hole portion and the second hole portion adjacent to each other is collected by the partition wall;

wherein the collection quantity measurement device further comprises:

an electromagnetic wave detector that detects the electromagnetic wave to be measured which has transmitted through the collector;

a reference value deriving unit that derives, based on a result detected by the electromagnetic wave detector, any one of an absorption rate, a group delay, and a dispersion of the electromagnetic wave to be measured in a reference area; and a collection quantity deriving unit that derives, based on the result detected by the electromagnetic wave detector and the result derived by the reference value deriving unit, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

19. The collection quantity measurement device according to claim 18, comprising:

a rotational drive unit that rotates the collector or a travel direction of the electromagnetic wave to be measured while a line in a direction perpendicular to the travel direction of the electromagnetic wave to be measured is set as a rotational axis; and a linear drive unit that moves the collector or the travel direction of the electromagnetic wave to be measured in a direction perpendicular to the travel direction of the electromagnetic wave to be measured and the rotational axis, wherein the detection is carried out by the electromagnetic wave detector while the rotational drive unit and the linear drive unit are operating.

20. The collection quantity measurement device according to claim 18, wherein:
   a line segment which is an intersection portion of a line perpendicular to an extension direction of the first, second, and third hole portions and the collector is contained in the reference area; and
   there are a plurality of the travel directions of the electromagnetic wave to be measured, and one of them is fixed along the line segment.

21. A collection quantity measurement method using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
   a first hole portion that is open at a first end on a side for receiving the gas, and is closed at a second end on a side opposite to the first end;
   a second hole portion that is closed at the first end, and is open at the second end; and
   a third hole portion that is closed at the second end, wherein:
   the first hole portion and the second hole portion are adjacent to each other;
   the third hole portions are adjacent to each other; and
   the material in the gas passing through a partition wall partitioning the first hole portion and the second hole portion adjacent to each other is collected by the partition wall;
   wherein the collection quantity measurement device further comprises an electromagnetic wave detector that detects the electromagnetic wave to be measured which has transmitted through the collector;
   wherein the collection quantity measurement method comprises:
   deriving a reference value by deriving, based on a result detected by the electromagnetic wave detector, any one of an absorption rate, a group delay, and a dispersion of the electromagnetic wave to be measured in a reference area; and
   deriving a collection quantity by deriving, based on the result detected by the electromagnetic wave detector and the reference value derivation, a weight or a density of the material present in an collection area, wherein:
   the reference area includes the third hole portion adjacent only to the third hole portion, and is on a side of the third hole portion with respect to a border between the third hole portion and the first or second hole portion; and
   the collection area is an area of the collector except for the reference area.

22. A collection quantity measurement method using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
   a first hole portion that is open at a first end on a side for receiving the gas, and is closed at a second end on a side opposite to the first end;
   a second hole portion that is closed at the first end, and is open at the second end; and
   a third hole portion that is closed between the first end and the second end, wherein:
   the first hole portion and the second hole portion are adjacent to each other;
   the third hole portions are adjacent to each other; and
   the material in the gas passing through a partition wall partitioning the first hole portion and the second hole portion adjacent to each other is collected by the partition wall;
   wherein the collection quantity measurement device further comprises an electromagnetic wave detector that detects the electromagnetic wave to be measured which has transmitted through the collector;
   wherein the collection quantity measurement method comprises:
   deriving a reference value by deriving, based on a result detected by the electromagnetic wave detector, any one of an absorption rate, a group delay, and a dispersion of the electromagnetic wave to be measured in a reference area; and
   deriving a collection quantity by deriving, based on the result detected by the electromagnetic wave detector and the reference value derivation, a weight or a density of the material present in an collection area, wherein:
   the reference area includes the third hole portion adjacent only to the third hole portion, and is on a side of the third hole portion with respect to a border between the third hole portion and the first or second hole portion; and
   the collection area is an area of the collector except for the reference area.

23. A computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:
   a first hole portion that is open at a first end on a side for receiving the gas, and is closed at a second end on a side opposite to the first end;
   a second hole portion that is closed at the first end, and is open at the second end; and
   a third hole portion that is closed at the second end, wherein:
   the first hole portion and the second hole portion are adjacent to each other;
   the third hole portions are adjacent to each other; and
   the material in the gas passing through a partition wall partitioning the first hole portion and the second hole portion adjacent to each other is collected by the partition wall;
   wherein the collection quantity measurement device further comprises an electromagnetic wave detector that detects the electromagnetic wave to be measured which has transmitted through the collector;
   wherein said collection quantity measurement process comprises:
   deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

24. A computer-readable medium having a program of instructions for execution by a computer to perform a collection quantity measurement process using a collection quantity measurement device having an electromagnetic wave output device that outputs an electromagnetic wave to be measured at a frequency equal to or higher than 0.01 [THz] and equal to or lower than 100 [THz] toward a collector which receives a gas, and collects a material in the gas, the collector comprising:

a first hole portion that is open at a first end on a side for receiving the gas, and is closed at a second end on a side opposite to the first end;

a second hole portion that is closed at the first end, and is open at the second end; and a third hole portion that is closed between the first end and the second end, wherein:

the first hole portion and the second hole portion are adjacent to each other;

the third hole portions are adjacent to each other; and the material in the gas passing through a partition wall partitioning the first hole portion and the second hole portion adjacent to each other is collected by the partition wall;

wherein the collection quantity measurement device further comprises an electromagnetic wave detector that detects the electromagnetic wave to be measured which has transmitted through the collector;

wherein said collection quantity measurement process comprises:

deriving a reference value by deriving, based on a result detected by the electromagnetic wave detector, any one of an absorption rate, a group delay, and a dispersion of the electromagnetic wave to be measured in a reference area; and deriving a collection quantity by deriving, based on the result detected by the electromagnetic wave detector and the reference value derivation, a weight or a density of the material present in an collection area, wherein:

the reference area includes the third hole portion adjacent only to the third hole portion, and is on a side of the third hole portion with respect to a border between the third hole portion and the first or second hole portion; and the collection area is an area of the collector except for the reference area.

* * * * *

UNITED STATES PATENT AND TRADEMARK OFFICE
CERTIFICATE OF CORRECTION

PATENT NO. : 8,210,035 B2  
APPLICATION NO. : 12/608282  
DATED : July 3, 2012  
INVENTOR(S) : M. Imamura et al.

Page 1 of 1

It is certified that error appears in the above-identified patent and that said Letters Patent is hereby corrected as shown below:

IN THE CLAIMS:

At column 21, line 55 (claim 8, line 9) "closed_at" should be -- closed at --.

At column 24, line 15 (claim 13, line 20) "hole_portion" should be -- hole portion --.

At column 24, line 49 (claim 14, line 11) "closed_at" should be -- closed at --.

Signed and Sealed this  
Twenty-second Day of January, 2013

David J. Kappos  
*Director of the United States Patent and Trademark Office*